US006737260B1

(12) United States Patent
Thomashow et al.

(10) Patent No.: US 6,737,260 B1
(45) Date of Patent: May 18, 2004

(54) SEQUENCES ENCODING PHZO AND METHODS

(75) Inventors: Linda S. Thomashow, Pullmn, WA (US); Shannon M. Delaney, Schiller Park, IL (US); Dmitri V. Mavrodi, Pullman, WA (US); David M. Weller, Pullman, WA (US)

(73) Assignees: The United States of America, as represented by the Secretary of Agriculture, Washington, DC (US); Washington State University Research Foundation, Pullman, WA (US)

( * ) Notice: Subject to any disclaimer, the term of this patent is extended or adjusted under 35 U.S.C. 154(b) by 146 days.

(21) Appl. No.: 09/965,175

(22) Filed: Sep. 27, 2001

Related U.S. Application Data

(60) Provisional application No. 60/236,634, filed on Sep. 29, 2000.

(51) Int. Cl.[7] .............................. C12N 9/02; C12N 15/53
(52) U.S. Cl. ............... 435/189; 435/252.3; 435/252.33; 435/252.34; 536/23.2
(58) Field of Search .............................. 435/189, 252.3, 435/252.33, 252.34; 536/23.2

(56) References Cited

U.S. PATENT DOCUMENTS 5,639,949 A * 6/1997 Ligon et al. ................ 800/20.5

OTHER PUBLICATIONS

Pierson III, L.S., et al. Mol. Plant–Microbiol. Interact 5(4), 330–339.*

Chin–A–Woeng, T.F.C. et al., Biocontrol by Phenazine–1–carboxamide–Producing *Pseudomonas chlororaphis* PCL1391 of Tomato Root Rot Caused by *Fusarium oxysporum f. sp. radicis–lycopersici*, Mol. Plant–Microbe Interact. (1998) 11(11):1069–1077.

Duffner, F.M. and R. Müller, "A novel phenol hydroxylase and catechol 2,3–dioxygenase from the thermophilic *Bacillus thermoleovarans* strain A2: nucleotide sequence and analysis of the genes," FEMS Microbiol. Lett. (1998) 161:37–45.

Galán, B., E. Diáz, M.A. Prieto, and J.L. Garcia, "Functional Analysis of the Small Component of the 4–Hydroxyphenylacetate 3–Monooxygenase of *Escherichia coli* W: a Prototype of a New Flavin:NAD(P)H Reductase Subfamily,"*J. Bacteriol.* (2000) 182(3):627–636.

Gibello, A., M. Suárez, and J.L. Allende, "Molecular Cloning and Analysis of the Genes Encoding the 4–hydroxyphenylacetate hydroxylase from *Klebsiella pneumoniae*," *Arch. Microbiol.* (1997) 167:166.

Hübner, A., C.E.Danganan, L. Xun, A.M. Chakrabarty, and W. Hendrickson, "Genes for 2,4,5–trichlorophenoxyacetic Acid Metabolism in *Burkholderia cepacia* AC1100: Characterization of the tftC and tftD Genes and Locations of the tft operons on Multiple Replicons," *Applied and Environmental Microbiology* (1998) 64(6):2086–2093.

Prieto, M.A. and J. L. Garcia, "Molecular Characterization of 4–Hydroxyphenylacetate 3–Hydroxylase of *Escherichia coli*," *Journal of Biological Chemistry* (1994) 269(36):22823–22829.

Takizawa, N., H. Yokoyama, K. Yanagihara, T. Hatta, and H. Kiyohara, "A Locus of *Pseudomonas pickettii* DTP0602, had, That Encodes 2,4,6–Trichlorophenol–4–Dechlorinase with Hydroxylase Activity, and Hydroxylation of Various Chlorophenols by the Enzyme," *J. Ferment. Bioeng.* (1995) 80(4):318–326.

Xun, L., and E.R. Sandvik, "Characterization of 4–Hydroxyphenylacetate 3–Hydroxylase (HpaB) of *Escherichia coli* as a Reduced Flavin Adenine Dinucleotide–Utilizing Monooxygenase," *Applied and Environmental Microbiology* (2000) 66(2):481–486.

* cited by examiner

*Primary Examiner*—Charles L. Patterson, Jr.
(74) *Attorney, Agent, or Firm*—Margaret A. Connor; John D. Fado

(57) ABSTRACT

The invention is directed to nucleic acid sequences which encode polypeptides having PhzO activity, namely, the ability to convert phenazine-1-carboxylic acid to a 2-hydroxylated phenazine, and isolated polypeptides having this activity. The invention is also directed to recombinant nucleic acid molecules, vectors, and host cells including the nucleic acid sequences as well as methods for producing and using the polypeptides, including expression in bacterial or plant cells to inhibit fungal pathogens.

8 Claims, 5 Drawing Sheets

SEQUENCE LISTING

<160> NUMBER OF SEQ ID NOS: 11

<210> SEQ ID NO 1
<211> LENGTH: 2869
<212> TYPE: DNA
<213> ORGANISM: Pseudomonas chlororaphis
<220> FEATURE:
<221> NAME/KEY: CDS
<222> LOCATION: (89)..(1564)
<223> OTHER INFORMATION:
<221> NAME/KEY: gene
<222> LOCATION: (76)..(1564)
<223> OTHER INFORMATION:
<221> NAME/KEY: RBS
<222> LOCATION: (76)..(81)
<223> OTHER INFORMATION:

<400> SEQUENCE: 1

```
tcgactctag aacgttgtcc ttgacccagc gatagacatc gggccagaac ctacataaac       60
aaagtcagac attactgagg ctgctacc atg cta gat ttt caa aac aag cgt         112
                                Met Leu Asp Phe Gln Asn Lys Arg
                                  1               5 aaa tat ctg aaa agt gca gaa tcc ttc aaa gct tca ctg cgt gat aac        160
Lys Tyr Leu Lys Ser Ala Glu Ser Phe Lys Ala Ser Leu Arg Asp Asn
   10                  15                  20 cgc act gtt att tat caa ggc caa gtt gtt gag gat gtg act aca cac        208
```

```
Arg Thr Val Ile Tyr Gln Gly Gln Val Val Glu Asp Val Thr Thr His
 25                  30                  35                  40 ttc tct acg gct gga ggc ata tcg caa gtt gca gaa atc tac gaa gaa        256
Phe Ser Thr Ala Gly Gly Ile Ser Gln Val Ala Glu Ile Tyr Glu Glu
                 45                  50                  55 caa ttc agc ggt gaa cac gac gac att ctg act tac gta cgc ccc gac        304
Gln Phe Ser Gly Glu His Asp Asp Ile Leu Thr Tyr Val Arg Pro Asp
             60                  65                  70 ggt tac ctg gcc tct tct gcc tat atg ccc cct aga aac aaa gaa gac        352
Gly Tyr Leu Ala Ser Ser Ala Tyr Met Pro Pro Arg Asn Lys Glu Asp
         75                  80                  85 ttg gcg tcg cga cgc cgc gca atc atg tac gtc tcg caa aaa acc tgg        400
Leu Ala Ser Arg Arg Arg Ala Ile Met Tyr Val Ser Gln Lys Thr Trp
     90                  95                 100 ggc acc cac tgc cgt aac ctg gac atg atc gcc agc ttc acc gtc ggc        448
Gly Thr His Cys Arg Asn Leu Asp Met Ile Ala Ser Phe Thr Val Gly
105                 110                 115                 120 atg atg gga tat ctg ccg aca ttc agg aaa aaa tgc cct gag tac gca        496
Met Met Gly Tyr Leu Pro Thr Phe Arg Lys Lys Cys Pro Glu Tyr Ala
                125                 130                 135 gaa aac att acc gaa tac cat gac tac gcc gag cgc aac agc ctg tat        544
Glu Asn Ile Thr Glu Tyr His Asp Tyr Ala Glu Arg Asn Ser Leu Tyr
            140                 145                 150 ttg tct gag acc att gtt gat cca cag ggc tat cgg gca cgt acc cac        592
Leu Ser Glu Thr Ile Val Asp Pro Gln Gly Tyr Arg Ala Arg Thr His
        155                 160                 165 ggc acc gac ctc aac ctg ccg ccg ccc gat cgt gcc gtg atg agg atc        640
Gly Thr Asp Leu Asn Leu Pro Pro Pro Asp Arg Ala Val Met Arg Ile
170                 175                 180 aac aag cag aac gcc gag ggc atc tgg atc agc ggc gtc aaa ggc gtg        688
Asn Lys Gln Asn Ala Glu Gly Ile Trp Ile Ser Gly Val Lys Gly Val
185                 190                 195                 200 ggc acg gca gca ccg cag tcc aat gaa ata ttt gtt ggc agc ttg ttc        736
Gly Thr Ala Ala Pro Gln Ser Asn Glu Ile Phe Val Gly Ser Leu Phe
                205                 210                 215 ccc gca gcg ccc gag gag tca ttc tgg gct tac gtc cct gtc gat gcg        784
Pro Ala Ala Pro Glu Glu Ser Phe Trp Ala Tyr Val Pro Val Asp Ala
            220                 225                 230 ccg ggg gtg aag att ttt tgc cga gag att gtc tcc cag cct cac gcc        832
Pro Gly Val Lys Ile Phe Cys Arg Glu Ile Val Ser Gln Pro His Ala
        235                 240                 245 agc gcc tat gac cac ccg ctc ata tcc aaa ggt gaa gaa gcc gag gcg        880
Ser Ala Tyr Asp His Pro Leu Ile Ser Lys Gly Glu Glu Ala Glu Ala
250                 255                 260 atg gtg gta ttc gat aac gtg ttc att cca cgc tgg cga atc atg gcg        928
Met Val Val Phe Asp Asn Val Phe Ile Pro Arg Trp Arg Ile Met Ala
265                 270                 275                 280 gcg aac gtg ccg gaa ctg gcc agc gcc ggc ttc ttc agt ctg tgg acc        976
Ala Asn Val Pro Glu Leu Ala Ser Ala Gly Phe Phe Ser Leu Trp Thr
                285                 290                 295 tca tac agc cat tgg tac acg ctc gtg cgc ctg gaa acc aag gct gac       1024
Ser Tyr Ser His Trp Tyr Thr Leu Val Arg Leu Glu Thr Lys Ala Asp
            300                 305                 310 ctg tat gcc gga ctg gcc aag gtg atc atg gaa gtc ctg ggc ctt gag       1072
Leu Tyr Ala Gly Leu Ala Lys Val Ile Met Glu Val Leu Gly Leu Glu
        315                 320                 325 ggg att gcg gtg gtt cgc cag cgg gtc agc gaa ata gtg cag ctt gcg       1120
Gly Ile Ala Val Val Arg Gln Arg Val Ser Glu Ile Val Gln Leu Ala
330                 335                 340
```

```
                                    -continued
gaa ata ctc aaa ggc atg tgc atc gcc tcc atc gaa acg gcc gag atg    1168
Glu Ile Leu Lys Gly Met Cys Ile Ala Ser Ile Glu Thr Ala Glu Met
345                 350                 355                 360 tcc gac ggc gac ata ttg ctg cct ggc cac aac gca ctg gcc gcc gga    1216
Ser Asp Gly Asp Ile Leu Leu Pro Gly His Asn Ala Leu Ala Ala Gly
                365                 370                 375 agg gtt ttt gcc atg gag aaa ttg cct cgg gtg ctg cat ttg ctc aga    1264
Arg Val Phe Ala Met Glu Lys Leu Pro Arg Val Leu His Leu Leu Arg
            380                 385                 390 gag ctg tgc gga cag ggc ttg atc ctc agg ttc aac gag aaa gac ttg    1312
Glu Leu Cys Gly Gln Gly Leu Ile Leu Arg Phe Asn Glu Lys Asp Leu
        395                 400                 405 gcc gcc gac gcc gcc ttt ggc cag aag ttc tcc tgg ttt ctt gac acg    1360
Ala Ala Asp Ala Ala Phe Gly Gln Lys Phe Ser Trp Phe Leu Asp Thr
    410                 415                 420 caa agc gtg ggc gcc aga gag aag aac ctg ctg atg aac cta gtg tgg    1408
Gln Ser Val Gly Ala Arg Glu Lys Asn Leu Leu Met Asn Leu Val Trp
425                 430                 435                 440 gac gtg gct gcc agt gag cac tcc aca cgt gca ttg gtg ttt gaa gaa    1456
Asp Val Ala Ala Ser Glu His Ser Thr Arg Ala Leu Val Phe Glu Glu
                445                 450                 455 cag cac gca ctc agc gag ccc ctg ctg cgc gat aac ctg gtg ctg gac    1504
Gln His Ala Leu Ser Glu Pro Leu Leu Arg Asp Asn Leu Val Leu Asp
            460                 465                 470 tac gac tac cgc gaa agc aca agc ctg ata cgc cgc cta gtg ggg ctc    1552
Tyr Asp Tyr Arg Glu Ser Thr Ser Leu Ile Arg Arg Leu Val Gly Leu
        475                 480                 485 aac gcc aaa tag acctgattgc cgtgtaggcg ccgcgcaacc cttcattcgt        1604
Asn Ala Lys
    490 gccgactgaa ctcggcacga atgaagggtt gtccgcctcc ggcccaggc atcccgtaag    1664 cttccaacct tcaacggtag tacaccgccc cattagcatc caaatgaata cggcaggagc    1724 ccgttacagc gctggcgctg gatgcctggc tacgcttgca caggatctcg gtccgagacg    1784 agccaggttt accggccccc ctttgttcga gccatgccac ttggcaggct cgttcagttg    1844 tagcggtcag cctgtcgccg gttggcttgc cacccgtacc gaacgtcagt agggcgcttg    1904 gtccgggtgg catccgggaa tgcagtgaaa cgcgtcgcct ggttccaggc ccaggcgcca    1964 gccaacggag aaaacaaggc gctcaccagc gcccatgcac acaggcgcgc gcgctttca    2024 ataccaaagc ccaagcccg tcacagcccc caagcgcca cctccaggcc agcgtccagc    2084 atcggccctc gcccagaagc gccagccata tcggcaccgt agcgaccagc gaaagggtca    2144 gcatgggccc gctcactgtt gtacattcct ccccacggac gacacatcat ttacccagtg    2204 aacggagttc aacgcgtgtt ctcgaccctc aatccgcgtc accgccggct tgccagtttc    2264 tcgttgctag ccgtggcctt aagcctcgcc gcctgcaacg cttccgcccc ttcccatacc    2324 gccctgcccc ccgccccgga aatcgcttgg ggttatcgca ccgacctgca agtgcagcac    2384 gccgaccggc atatgcggc gcggccaac ccgttggcgg ccgaagccgg gcgcgaaatg    2444 ttgcgcaagg gtggttcggc catcgatgcg gcgattgcca tgcaagcggt gctgaccctg    2504 gtggagccgc agtcgtcggg gatcggcggc ggcgccttga tcgtgctctg ggacggcaag    2564 gcggtgcgca cgtacgacgg tcgcgaaacc gcgccggccg gggccaccga aaagttgttc    2624 ctgcaagccg acggcaagcc catgccgttc cccaggcac agatcggcgg ccgttcggtg    2684 ggtacgcccg gcgtgctgcg cgccctggaa ctgcccatg aaaaacacgg ccgcctgccg    2744 tgggcgcagc tgttcgagcc ggcgattcgc ctggcggacc agggtttccc gatctccccg    2804
```

-continued

```
cgcctgcaca gcatgataaa aaccgatccg tacctggcga aatcgccgga tatggccgcc    2864
tactt                                                                2869
```

<210> SEQ ID NO 2
<211> LENGTH: 491
<212> TYPE: PRT
<213> ORGANISM: Pseudomonas chlororaphis

<400> SEQUENCE: 2

```
Met Leu Asp Phe Gln Asn Lys Arg Lys Tyr Leu Lys Ser Ala Glu Ser
1               5                   10                  15

Phe Lys Ala Ser Leu Arg Asp Asn Arg Thr Val Ile Tyr Gln Gly Gln
            20                  25                  30

Val Val Glu Asp Val Thr Thr His Phe Ser Thr Ala Gly Gly Ile Ser
        35                  40                  45

Gln Val Ala Glu Ile Tyr Glu Glu Gln Phe Ser Gly Glu His Asp Asp
    50                  55                  60

Ile Leu Thr Tyr Val Arg Pro Asp Gly Tyr Leu Ala Ser Ser Ala Tyr
65                  70                  75                  80

Met Pro Pro Arg Asn Lys Glu Asp Leu Ala Ser Arg Arg Ala Ile
                85                  90                  95

Met Tyr Val Ser Gln Lys Thr Trp Gly Thr His Cys Arg Asn Leu Asp
            100                 105                 110

Met Ile Ala Ser Phe Thr Val Gly Met Met Gly Tyr Leu Pro Thr Phe
        115                 120                 125

Arg Lys Lys Cys Pro Glu Tyr Ala Glu Asn Ile Thr Glu Tyr His Asp
    130                 135                 140

Tyr Ala Glu Arg Asn Ser Leu Tyr Leu Ser Glu Thr Ile Val Asp Pro
145                 150                 155                 160

Gln Gly Tyr Arg Ala Arg Thr His Gly Thr Asp Leu Asn Leu Pro Pro
                165                 170                 175

Pro Asp Arg Ala Val Met Arg Ile Asn Lys Gln Asn Ala Glu Gly Ile
            180                 185                 190

Trp Ile Ser Gly Val Lys Gly Val Gly Thr Ala Ala Pro Gln Ser Asn
        195                 200                 205

Glu Ile Phe Val Gly Ser Leu Phe Pro Ala Ala Pro Glu Glu Ser Phe
    210                 215                 220

Trp Ala Tyr Val Pro Val Asp Ala Pro Gly Val Lys Ile Phe Cys Arg
225                 230                 235                 240

Glu Ile Val Ser Gln Pro His Ala Ser Ala Tyr Asp His Pro Leu Ile
                245                 250                 255

Ser Lys Gly Glu Glu Ala Glu Ala Met Val Val Phe Asp Asn Val Phe
            260                 265                 270

Ile Pro Arg Trp Arg Ile Met Ala Ala Asn Val Pro Glu Leu Ala Ser
        275                 280                 285

Ala Gly Phe Phe Ser Leu Trp Thr Ser Tyr Ser His Trp Tyr Thr Leu
    290                 295                 300

Val Arg Leu Glu Thr Lys Ala Asp Leu Tyr Ala Gly Leu Ala Lys Val
305                 310                 315                 320

Ile Met Glu Val Leu Gly Leu Glu Gly Ile Ala Val Val Arg Gln Arg
                325                 330                 335

Val Ser Glu Ile Val Gln Leu Ala Glu Ile Leu Lys Gly Met Cys Ile
            340                 345                 350
```

```
Ala Ser Ile Glu Thr Ala Glu Met Ser Asp Gly Asp Ile Leu Leu Pro
        355                 360                 365

Gly His Asn Ala Leu Ala Ala Gly Arg Val Phe Ala Met Glu Lys Leu
    370                 375                 380

Pro Arg Val Leu His Leu Leu Arg Glu Leu Cys Gly Gln Gly Leu Ile
385                 390                 395                 400

Leu Arg Phe Asn Glu Lys Asp Leu Ala Ala Asp Ala Ala Phe Gly Gln
                405                 410                 415

Lys Phe Ser Trp Phe Leu Asp Thr Gln Ser Val Gly Ala Arg Glu Lys
            420                 425                 430

Asn Leu Leu Met Asn Leu Val Trp Asp Val Ala Ala Ser Glu His Ser
        435                 440                 445

Thr Arg Ala Leu Val Phe Glu Glu Gln His Ala Leu Ser Glu Pro Leu
    450                 455                 460

Leu Arg Asp Asn Leu Val Leu Asp Tyr Asp Tyr Arg Glu Ser Thr Ser
465                 470                 475                 480

Leu Ile Arg Arg Leu Val Gly Leu Asn Ala Lys
                485                 490
```

<210> SEQ ID NO 3
<211> LENGTH: 20
<212> TYPE: DNA
<213> ORGANISM: artificial sequence
<220> FEATURE:
<223> OTHER INFORMATION: primer PCA2a

<400> SEQUENCE: 3
ttgccaagcc tcgctccaac                                            20

<210> SEQ ID NO 4
<211> LENGTH: 20
<212> TYPE: DNA
<213> ORGANISM: artificial sequence
<220> FEATURE:
<223> OTHER INFORMATION: primer PCA3b

<400> SEQUENCE: 4
ccgcgttgtt cctcgttcat                                            20

<210> SEQ ID NO 5
<211> LENGTH: 21
<212> TYPE: DNA
<213> ORGANISM: artificial sequence
<220> FEATURE:
<223> OTHER INFORMATION: primer 30-84XBA

<400> SEQUENCE: 5
aagtccagat gcgaaagaac g                                          21

<210> SEQ ID NO 6
<211> LENGTH: 21
<212> TYPE: DNA
<213> ORGANISM: artificial sequence
<220> FEATURE:
<223> OTHER INFORMATION: primer PHZO10

<400> SEQUENCE: 6
aagtggcatg gctcgaataa a                                          21

<210> SEQ ID NO 7
<211> LENGTH: 17
<212> TYPE: DNA

```
<213> ORGANISM: artificial sequence
<220> FEATURE:
<223> OTHER INFORMATION: primer PHZ1

<400> SEQUENCE: 7
ggcgacatgg tcaacgg                                                    17

<210> SEQ ID NO 8
<211> LENGTH: 17
<212> TYPE: DNA
<213> ORGANISM: artificial sequence
<220> FEATURE:
<223> OTHER INFORMATION: primer PHZ2

<400> SEQUENCE: 8
cggctggcgg cgtattc                                                    17

<210> SEQ ID NO 9
<211> LENGTH: 26
<212> TYPE: DNA
<213> ORGANISM: artificial sequence
<220> FEATURE:
<223> OTHER INFORMATION: primer PHZX

<400> SEQUENCE: 9 tttttcata tgcctgcttc gctttc                                           26

<210> SEQ ID NO 10
<211> LENGTH: 28
<212> TYPE: DNA
<213> ORGANISM: artificial sequence
<220> FEATURE:
<223> OTHER INFORMATION: primer PHZY

<400> SEQUENCE: 10
tttggatcct taagttggaa tgcctccg                                        28

<210> SEQ ID NO 11
<211> LENGTH: 25
<212> TYPE: DNA
<213> ORGANISM: artificial sequence
<220> FEATURE:
<223> OTHER INFORMATION: primer PHZO

<400> SEQUENCE: 11
cgactctaga acgttgtcct tgacc                                           25
```

SEQUENCES ENCODING PHZO AND METHODS

CROSS-REFERENCE TO RELATED APPLICATIONS

This application claims the benefit of U.S. Provisional Application No. 60/236,634 filed Sep. 29, 2000. The disclosure of said provisional application is incorporated herein by reference in its entirety.

BACKGROUND OF THE INVENTION

1. Field of the Invention

The present invention relates to (a) nucleic acid sequences which encode polypeptides having PhzO activity, that is, the ability to convert phenazine-1-carboxylic acid to 2-hydroxylated phenazines and (b) isolated polypeptides having this activity. The invention also relates to recombinant nucleic acid molecules, vectors, and host cells comprising the nucleic acid sequences as well as methods for producing and using the polypeptides, including expression in bacterial or plant cells to inhibit fungal pathogens.

2. Description of the Art

Root diseases caused by *Gaeumannomyces graminis*, Rhizoctonia, and Pythium and diseases caused by the pathogenic fungus Fusarium cause a significant adverse impact on the production of important crops worldwide. The root disease take-all, caused by *Gaeumannomyces graminis* var. *tritici* (Ggt), Rhizoctonia root rot, caused by *Rhizoctonia solani* and *R. oryzae*, and Pythium root rot caused by any of several Pythium species, notably, *Pythium ultimum* and *P. irregulare*, are important root diseases of small grain crops, e.g., wheat, barley, triticale, and rye, worldwide. *Fusarium graminearum* (Schwabe) and *Fusarium culmorum* are the primary causal agents of a disease known as Fusarium head blight, head blight, or scab, of wheat, barley, oats and rye. *Fusarium solani* causes root and crown rots, and *Fusarium oxysporum* causes wilts.

Widespread diseases of small grain crops and turf grass are caused by the soil-borne fungus *Gaeumannomyces graminis* (Gg), a member of the ascomycota class of fungi, and result in significant economic losses due to reductions in crop yield. Take-all, a disease caused by *Gaeumannomyces graminis* var. *tritici* (Ggt) occurs in all wheat-growing regions of the world and is probably the most important root disease of wheat and related small grains worldwide. Symptoms of wheat take-all include dark longitudinal lesions on roots; in severe cases, the entire root may become blackened with disease with the fungus migrating to in the crown of the wheat plant (where the crown roots originate) and the tillers (stems). Severely infected wheat plants are identified in the field by their white heads which result when infection of the crown by the fungus cuts off water transport to upper plant parts causing the plant to die prematurely. Yield losses can be considerable, up to 50% of the potential wheat yield. There are no resistant wheat cultivars, and registered fungicides perform inconsistently. Further, growers are being increasingly challenged to grow wheat with minimum or no tillage to reduce soil erosion. These practices increase the severity of take-all and other root diseases. Although wheat is particularly susceptible to the take-all fungus, many other Gramineae such as barley, rye, and triticale can also be infected.

Traditionally, take-all has been controlled by a combination of crop rotation and tillage, practices which reduce the inoculum potential of the pathogen. However, because long rotations are often not economically feasible and tillage contributes to soil erosion, the trend in cereal production is toward less tillage and two or three wheat crops before a break. Both of these practices exacerbate take-all. There is no known source of genetic resistance in wheat against take-all, and methods of chemical control are limited. The need for agriculture to become more sustainable and less dependent on chemical pesticides has necessitated the development of alternative approaches to control take-all and other soil-borne diseases.

Other Gg fungi, for example, *Gaeumannomyces graminis* var. *avenae* (Gga), infect oats and grasses and have been identified as causing take-all patch in turf grasses such as bent grass. *Gaeumannomyces graminis* var. *graminis* (Ggg) infects some grasses and has been suggested as causing crown sheath rot in rice.

Rhizoctonia, a member of the basidiomycota class of fungi, causes root and stem rot on most food, fiber, and ornamental plants throughout the world, including small grain crops, turf grass, asparagus, canola, corn, sugarbeet, tomatoes, potatoes, peas, rice, beans, soybeans, strawberries, zucchini, and cotton. Root rot on small grain crops caused by Rhizoctonia occurs throughout the United States Pacific Northwest, in Australia, and South Africa, and potentially throughout the temperate regions of the world wherever small grains are grown, especially if grown with reduced or no-tillage (direct drilling). Rhizoctonia root rot caused by *R. solani* AG8 begins as brown cankerous lesions on the seminal and crown roots that eventually girdles and then severs the roots. Plants with roots pruned off by this disease remain stunted and eventually die without making heads. The disease tends to affect plants in patches and has given rise to other names, such as bare patch disease, purple patch, crater disease, and barley stunt disorder. Of all small grain crops, barley is especially susceptible to *R. solani* AG8. *Rhizoctonia oryzae* infects the embryos of germinating seeds, preventing germination or limiting the formation of seminal roots to only one or two when healthy seedlings produce five or six seminal roots. These two Rhizoctonia species, together with *Rhizoctonia cerealis* and possibly other Rhizoctonia species occur as different mixtures, depending on the soil, cropping systems, weed management practices, and possibly other factors not yet identified.

The soil-borne pathogen complex of Pythium spp. comprises a group of fungi that are among the most successful of all microbial colonists in agricultural soils. It is estimated that nearly all cultivated soil in the world contains spores of at least one, two, three, and even as high as ten Pythium species. Pythium, a member of the oomycetes class of fungi, like Rhizoctonia, affects virtually all food, fiber, and ornamental plants throughout the world. Examples of these plants are given above. Pythium damage to small grains begins as embryo infections and associated poor emergence or stand establishment and continues as destruction of the fine lateral rootlets and root hairs. Plants with Pythium root rot have the appearance of plants without enough fertilizer, because the disease limits the absorptive capacity of the root system through destruction of fine rootlets and root hairs. There are several species of Pythium with ability to attack cereals, either embryos of germinating seeds, root tips and fine rootlets, or all of these delicate and usually juvenile or meristematic tissues.

Fusarium head blight or scab is a fungal disease of wheat, barley, oats, rye, and wheatgrasses that affects both grain yield and quality. It occurs worldwide, particularly when temperatures and humidity favor the proliferation of the causal agent, *Fusarium graminearum*, at the time of heading. Head blight has caused losses in the billions of dollars to United States and Canadian growers and processors within this decade. Yield and grain quality losses of wheat due to Fusarium head blight approached one billion dollars in Minnesota, North Dakota, and South Dakota in 1993 and 200–400 million dollars across the region in subsequent years. Losses were in excess of 300 million dollars in Ohio, Michigan, Indiana, and Illinois in 1995 and 1996. Quality of grain is also compromised since infected grain is usually contaminated with a mycotoxin, vomitoxin or DON, produced by the fungus that is detrimental to humans and livestock. In addition, the disease has threatened barley production in the upper Midwest because brewers have imposed zero tolerance limits for vomitoxin in grain.

Certain strains of root-colonizing fluorescent Pseudomonas spp. have gained attention in recent years because they produce broad-spectrum antibiotic metabolites that can provide protection against various soilborne root pathogens (Thomashow and Weller, pp. 187–235. In G. Stacey and N. T. Keen (ed.), *Plant-Microbe Interactions*. Chapman and Hall, New York, N.Y., 1996). One such class of antibiotics, the phenazines, encompasses a large family of heterocyclic nitrogen-containing compounds produced in late exponential and stationary phase. The ability to produce phenazines is limited almost exclusively to bacteria, and has been reported in members of the genera Pseudomonas, Streptomyces, Nocardia, Sorangium, Brevibacterium, and Burkholderia (Turner and Messenger, *Advances in Microbial Physiol.* 27: 211–275, 1986). There are currently over 50 known phenazine compounds with the same basic structure, differing only in the derivatization of the heterocyclic core. These modifications largely determine the physical properties of phenazines and influence their biological activity against plant and animal pathogens.

The broad-spectrum activity exhibited by phenazine compounds against fungi and other bacteria is not understood. It is thought that they can diffuse across the membrane and, once inside the cell, accept a single electron, disrupting respiration by interfering with the normal process of electron transport. This results in the overproduction of $O_2^-$ and $H_2O_2$, which overwhelm cellular superoxide dismutases and ultimately cause cell death. The cellular superoxide dismutases in *P. aeruginosa*, which produces the phenazine compound pyocyanin, are more active than those of phenazine-non-producing bacteria such as *Escherichia coli*, and they provide protection against phenazines (Hassan and Fridovich,*J. Bacteriol.* 141:156–163, 1980; Hassett et at.,*J. Bacteriol.* 177:6330–6337, 1995).

Several studies conducted in the early 1970s revealed tight links between phenazine biosynthesis and the shikimic acid pathway (Turner and Messenger, 1986, supra), but the biochemistry and genetic control of phenazine synthesis are still not fully understood. Chorismic acid has long been recognized as the branchpoint from the shikimic acid pathway to phenazine synthesis (Longley et al., *Can. J. Microbiol.* 18:1357–1368, 1972). Studies with radiolabeled precursors suggest that the phenazine core is formed by the symmetrical condensation of two molecules of chorismic acid (Chang et al., *Can. J. Microbiol.* 72:581–583, 1969; Herbert et al., *Tetrahedron Letters* 8:639–642, 1976; Hollstein and McCamey, *J. Org. Chem.* 38:3415–3417, 1973; Longley et al., 1972, supra), while the amide nitrogen of glutamine serves as the immediate source of nitrogen in the heterocyclic nucleus of phenazine compounds (Römer and Herbert, *Z. Naturforsch.* C 37:1070–1074, 1982). Phenazine-1,6-dicarboxylic acid is the first phenazine formed, and it is thought to be converted to phenazine-1-carboxylic acid (PCA), a key intermediate in the synthesis of other phenazines by fluorescent pseudomonads (Bying and Turner, *J. Gen. Microbiol.* 97:57–62, 1976; Herbert et al., 1976, supra; Hollstein and McCamey, 1973, supra; Messenger and Turner, *FEMS Microbiol. Lett.* 18:65–68, 1983).

Genetic studies in fluorescent Pseudomonas spp., the only microorganisms for which the genes responsible for the assembly of the heterocyclic phenazine nucleus have been cloned and sequenced, support this model. The phenazine biosynthetic loci from *P. fluorescens* 2–79 (Mavrodi et al.,*J. Bacteriol.* 180:2541–2548, 1998), *P. aureofaciens* [synonym: *P. chlororaphis*] 30–84 (Mavrodi et al., 1998, supra; Pierson III et al., *FEMS Microbiol. Lett.* 143:299–307, 1995), *P. aeruginosa* PA01 (D. V. Mavrodi and L. S. Thomashow, unpublished), and *P. chlororaphis* PCL1391(Chin-A-Woeng et al., *Pseudomonas '99: Biotechnology and Pathogenesis*, S48, Maui, Hi., 1999) are highly conserved. Each contains a seven-gene core operon regulated in a cell-density dependent manner by homologues of LuxI and LuxR (D. V. Mavrodi and S. K. Farrand, unpublished; Latifi et al., *Mol. Microbiol.* 17:333–343, 1995; Wood and Pierson III, *Gene* 108:49–53, 1996). In *P. fluorescens* 2–79, *P. aureofaciens* 30–84, and *P. chlororaphis* PCL1391, the phzI/R genes are found directly upstream from the phenazine core. Phenazine production in *Pseudomonas aeruginosa* is controlled by two sets of regulatory proteins, rhlI/R and lasI/R, located elsewhere in the genome. The core gene products PhzC, PhzD, and PhzE, which are homologous with PhzF, PhzA, and PhzB in strain 30–84, are similar to enzymes of shikimic and chorismic acid metabolism. Sequence comparisons of PhzD and PhzE with other chorismate-modifying enzymes have shed new light on probable intermediates in the PCA pathway, suggesting that phenazine synthesis proceeds via the intermediates aminodeoxyisochorismic acid and 3-hydroxyanthranilate (Mavrodi et al., 1998, supra) rather than anthranilate, as suggested previously (Essar et al., *J. Bacteriol.* 172:884–900, 1990). It should be noted that *P. aureofaciens* strains are also known as *P. chlororaphis*. In cases where the cited references use the term *P. aureofaciens*, this designation has been retained.

Although the phenazine biosynthetic loci of fluorescent pseudomonads are highly homologous, individual species typically differ in the range of phenazine compounds they produce. Previous work by Pierson et al., 1995, supra, suggested that the phzC gene of *P. aureofaciens* 30–84, and in particular the last 28 amino acids of the PhzC protein, are essential for the production 2-hydroxyphenazine-1-carboxylic acid (2-OH-PCA) and 2-hydroxyphenazine (2-OH-PHZ), derivatives characteristic of strains previously designated *P. aureofaciens* but now classified as *P. chlororaphis* (Johnson and Palleroni, *Inter. J. Syst. Bacteriol.* 39:230–235, 1989).

Phenazine product specificity directed to compounds having biocontrol activity or active in the biosynthesis of phenazines having biocontrol activity and transformed microorganisms and plants producing such compounds can provide an important resource for control of plant disease or lead to the development of novel pharmaceutical products.

SUMMARY OF THE INVENTION

The present invention is directed to phzO nucleic acid sequences which encode polypeptides having PhzO activity, that is, the ability to convert phenazine-1-carboxylic acid to a 2-hydroxylated phenazine. The invention is further directed to isolated polypeptides having PhzO activity. The invention also relates to recombinant nucleic acid molecules, vectors, and host cells comprising the nucleic acid sequences as well as methods for producing and using the polypeptides, including expression in bacterial or plant cells to inhibit fungal pathogens.

More particularly, the invention encompasses isolated nucleic acid molecules that encode PhzO polypeptides. The phzO gene sequence is specifically exemplified herein. As discussed in detail below, the novel gene designated phzO was located 271 nucleotides downstream from phzD, in the core phenazine operon phzXYFABCD of *P. aureofaciens* 30–84, and was preceded by a well-conserved potential ribosome binding site, GAGG. phzO encoded a 491-amino acid protein with a calculated molecular mass of 55.1 kDa. Homology searches with the deduced amino acid sequence revealed similarity to bacterial aromatic hydroxylases and monooxygenases (Table 3). Phylogenetic analysis of these aligned protein sequences resulted in the tree shown in FIG. 3. The high bootstrap values (from 1,000 resamplings) showed the robustness of these groups.

As shown in detail, below, results of our study show clearly that phzXYFABCD, the core phenazine biosynthetic operon of strain 30–84, is responsible only for the synthesis of phenazinc-1-carboxylic acid (PCA). When transformed with these genes, the sole phenazine product synthesized by *P. fluorescens* strains Q8r1-96 and M4-80R (which themselves do not produce phenazines) was phenazine-1-carboxylic acid. However, phenazine-non-producing strains transformed with phzXYFABCD and phzO, or *P. fluorescens* 2–79 transformed with phzO, synthesized hydroxyphenazine compounds in addition to phenazine-1-carboxylic acid, and *E. coli* expressing phzO rapidly converted exogenously-supplied phenazine-1-carboxylic acid to 2-hydroxylated phenazine products. Finally, a mutant of 30–84 inactivated in phzO produced only phenazine-1-carboxylic acid.

Nucleic acid sequences which hybridize specifically to the coding sequence or its complement under medium or high stringency conditions and which encode a polypeptide having PhzO activity are also encompassed by the present invention.

Nucleic acid sequences having at least 50% sequence identity with the exemplified phzO sequence as described in detail, below, and which encode a polypeptide having PhzO activity are also encompassed by the present invention.

The present invention is also directed to isolated polypeptides having PhzO activity. A polypeptide having an amino acid sequence which has at least 60% sequence identity with the exemplified PhzO polypeptide as described in detail, below, is encompassed by the invention. Polypeptides encoded by a nucleic acid sequence which hybridizes under medium or high stringency conditions with exemplified nucleic acid sequences as discussed in detail, below, are also encompassed by the invention. Variants of the polypeptides are encompassed by the invention as well as fragments having PhzO activity.

A further aspect of the invention is the provision of recombinant nucleic acid molecules containing the sequences encoding polypeptides having PhzO activity. Such molecules include, for example, recombinant vectors, such as cloning, expression or transformation vectors, which contain a DNA sequence encoding a polypeptide having PhzO activity.

Another aspect of the invention is the provision of cells which are transformed by the above vectors or DNA sequences. A particular use of the invention is the provision of bacterial cells transformed with a nucleic acid sequence encoding a polypeptide having PhzO activity to provide bacterial strains which produce PhzO.

In one aspect of the invention, microorganism strains which produce phenazines such as phenazine-1-carboxylic acid are transformed with a nucleic acid sequence which encodes for a polypeptide having PhzO activity, to thereby obtain transformed strains which produce a 2-hydroxylated phenazine or which produce increased amounts of a 2-hydroxylated phenazine.

In another aspect of the invention, phenazine non-producing microorganism strains are transformed with a phz operon capable of producing phenazine-1-carboxylic acid and a nucleic acid sequence which encodes for a polypeptide having PhzO activity, to thereby obtain transformed strains which produce a 2-hydroxylated phenazine.

In another aspect of the invention, microorganism strains which contain a nucleic acid sequence which encodes for a polypeptide having PhzO activity are fed an exogenous phenazine compound such as phenazine-1-carboxylic acid to produce a 2-hydroxylated phenazine.

The invention is also directed to biologically pure cultures of the microorganism strains described above. A particular use of the strains is to suppress (inhibit the incidence of or reduce the incidence or severity of) or control fungal diseases, for example, soilborne plant root diseases.

A further aspect of the invention is application of the strains of the invention or compositions comprising the strains. For example, the strains or compositions comprising the strains can be used as a seed, soil, furrow treatment or drench, for application to suppress or control fungal disease.

Another aspect of the invention is the provision of plant cells transformed with a nucleic acid sequence encoding a polypeptide having PhzO activity to provide transformed plants which produce PhzO, to provide plants having resistance or enhanced resistance to fungal diseases. In one embodiment, plants containing a nucleic acid sequence which encodes for a polypeptide having PhzO activity are supplied with an exogenous source of phenazine-1-carboxylic acid (of chemical or microbial origin) to produce a 2-hydroxylated phenazine.

A further aspect of the invention is the provision of oligonucleotide probes capable of detecting a phzO gene or functional equivalents thereof, and the use of the probes to isolate nucleic acid sequences encoding a phzO gene or functional equivalent thereof. The nucleic acid sequences which specifically hybridize to the probes and which encode a functional polypeptide having PhzO activity are encompassed by the present invention.

Using the nucleic acid sequences of the invention facilitates the isolation of homologous genes from microorganisms to obtain genes which protect host cells, including bacteria, and plants against fungal pathogens.

The invention is also directed to methods of producing and using the polypeptides of the invention, and to methods of producing 2-hydroxylated phenazines.

Other objects and advantages of the invention will become readily apparent from the ensuing description.

BRIEF DESCRIPTION OF THE SEQUENCES

Figure 1:
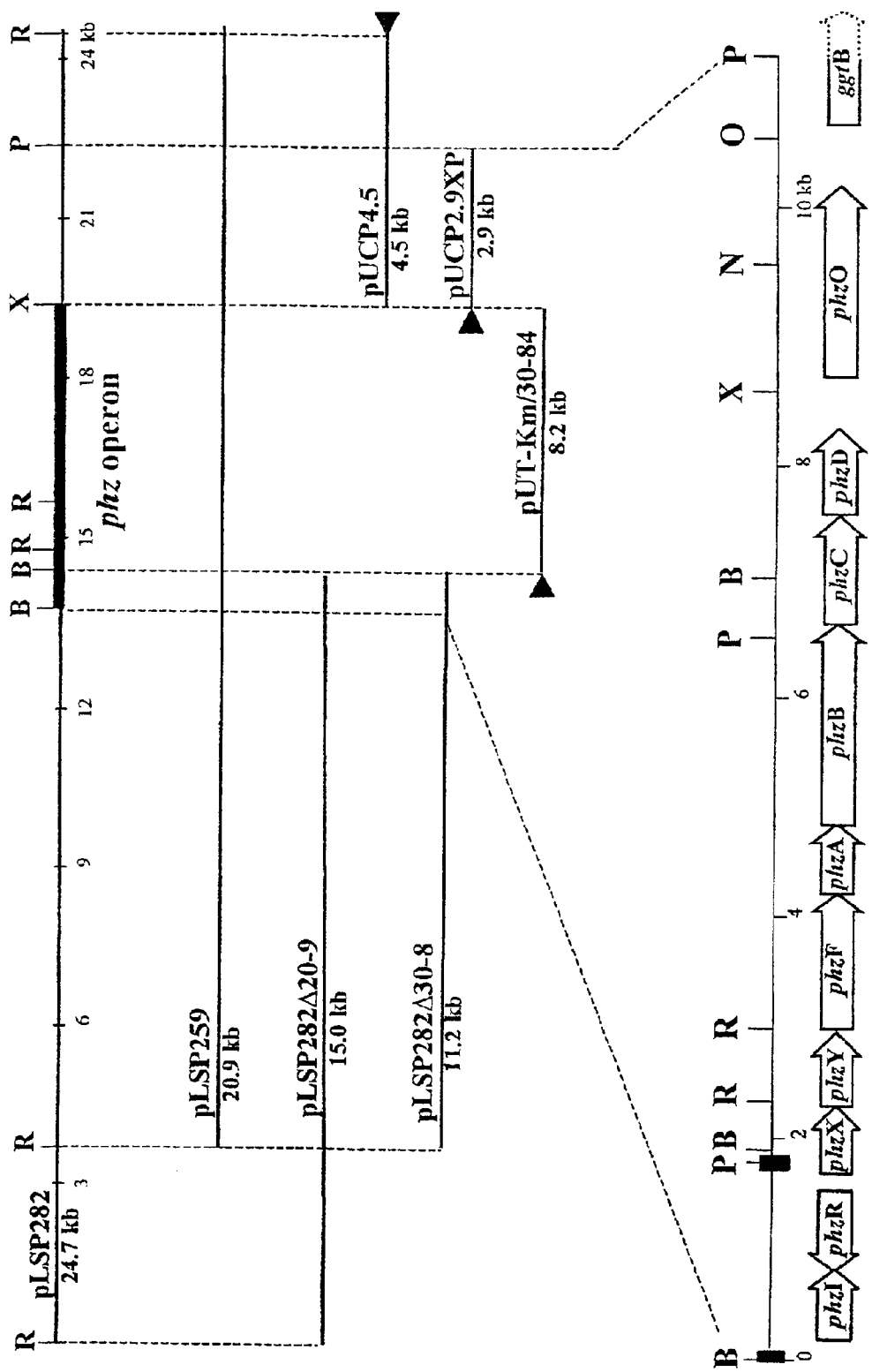
FIG. 1 shows the physical map of the phenazine biosynthetic region (phzIRXYFABCD and phzO) from *P. aureofaciens* 30–84 and the constructs used herein. The phenazine operon was described previously (Pierson et al., 1995, supra). The lux boxes are represented by ■. ▶ indicates the promoters from pUT-Km and pUCP26 used in subcloning. ggt indicates the position of an open reading frame with similarity to gamma-glutamyltranspeptidase. The restriction enzymes indicated on map are B, BglII; N, NcoI; O, NotI; P, PstI; R, EcoRI; and X, XbaI.

SEQ ID NO:1 is the nucleotide sequence for the phzO gene.

SEQ ID NO:2 is the PhzO polypeptide encoded by SEQ ID NO:1.

SEQ ID NO:3 is primer PCA2a.

SEQ ID NO:4 is primer PCA3b.

SEQ ID NO:5 is primer 30–84XBA.

SEQ ID NO:6 is primer PHZO10.

SEQ ID NO:7 is primer PHZ1.

SEQ ID NO:8 is primer PHZ2.

SEQ ID NO:9 is primer PHZX.

SEQ ID NO:10 is primer PHZY.

SEQ ID NO:11 is primer PHZO.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton, et al., Dictionary of Microbiology and Molecular Biology (2d ed. 1994); The Cambridge Dictionary of Science and Technology (Walker ed., 1988); The Glossary of Genetics, 5th Ed., Rieger, R., et al.(eds.), Springer Verlag (1991); and Hale & Marham, The Harper Collins Dictionary of Biology (1991).

To facilitate understanding of the invention, a number of terms are defined below.

"Phenazine" refers to heterocyclic nitrogen-containing compounds with the general formula

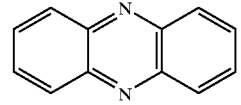

formula (Turner and Messenger, 1986, supra).

The phenazine biosynthetic (phz) locus is localized in *P. fluorescens* 2–79 within a 8,505-bp BglII-XbaI DNA fragment, and consists of 9 genes designated as phzABCDEFG,5 phzI and phzR. The complete sequence of the phz locus from *P. fluorescens* 2–79 is listed in the GenBank computer database under the accession number L48616. The phzABCDEFG genes are organized in a single operon and are responsible for phenazine-1-carboxylic acid production in *P. fluorescens* 2–79. Strain *P. fluorescens* 2–79 is available from the NRRL Patent Depository as NRRL B-15132. Other fluorescent Pseudomonas spp. which produce the antibiotic phenazine-1-carboxylic acid have been fully described in the literature and are available from depositories. See, for example, Raaijmakers et al., *Applied and Environmental Microbiology* 63:881–887 (1997), which describes phenazine-1-carboxylic acid-producing Pseudomonas species. Raaijmakers et al. further describe primer PCA2a (TTGCCAAGCCTCGCTCCAAC) (SEQ ID NO:3) and primer PCA3b (CCGCGTTGTTCCTCGTTCAT) (SEQ ID NO:4) and probes which can be used to detect phenazine-producing strains or retrieve the phenazine biosynthetic genes using standard techniques. The authors also show conservation of phenazine genes among Pseudomonas strains of worldwide origin (see FIG. 2 of Raaijmakers et al.). Further documentation of conservation of phenazines is provided in Mavrodi et al., 1998, supra.

As discussed above, products of the phzC, phzD, and phzE genes share similarities with enzymes of shikimic acid and chorismic acid metabolism and, together with PhzF, are absolutely necessary for PCA production. PhzG is similar to pyridoxamine-5'-phosphate oxidases and probably is a source of cofactor for phenazine-1-carboxylic acid-synthesizing enzyme(s). Products of the phzA and phzB genes are highly homologous to each other and may be involved in stabilization of a putative phenazine-1-carboxylic acid-synthesizing multienzyme complex.

phzABCDEFG, phzX, and phzY are described in detail in Mavrodi et al., 1998, supra. phzx and phzY are homologous to phzA and phzB. phzX and phzY are described in the GenBank computer database under the accession number AF007801.

Pierson et al., 1995, supra, describes a DNA sequence of five contiguous open reading frames which the authors named as phzF, phzA, phzB, phzC, and phzD, and which is described in GenBank accession number L48339, denoted as encoding phenazine biosynthesis in *Pseudomonas aureofaciens* 30–84.

The accepted nomenclature for the phz biosynthetic locus is phzABCDEFG as identified in GenBank accession number L48616. Pierson et al., 1995, supra uses different nomenclature for their 5-gene locus. The Pierson et al. 5-gene *P. aureofaciens* 30–84 genes denoted as phzF, phzA, phzB, phzC, and phzD are homologous to *P. fluorescens* 2–79 genes phzC, phzD, phzE, phzF and phzG. In tabular form, the nomenclature is:

| Pierson et al. |   |   | F | A | B | C | D |
|---|---|---|---|---|---|---|---|
| Mavrodi et al. | A | B | C | D | E | F | G |

The functional tests for phenazine production are described in the literature and include several common analytical techniques, such as UV-spectroscopy, thin-layer chromatography (TLC), and high-pressure liquid chromatography (HPLC) (see Mavrodi, 1998, supra; Thomashow and D. M. Weller, *Journal of Bacteriology* 170:3499–3508, 1988; and Pierson III and Thomashow, 1992, supra).

"PhzO" refers to an aromatic monooxygenase protein or polypeptide having the ability to produce at least one 2-hydroxylated phenazine from phenazine-1-carboxylic acid. Exemplary 2-hydroxylated phenazines include 2-hydroxyphenazine-1-carboxylic acid and 2-hydroxyphenazine. A HPLC protocol for detection of phenazine metabolites is described in detail, below. A fungal inhibition assay to determine inhibition of growth of *Gaeumannomyces graminis* var. *tritici* by phenazines produced by microorganism strains is described by Ownley et al., *Phytopathology* 82:178–184, 1992, and described in the Example, below.

The term "transgenic" when used in reference to a cell refers to a cell which contains a transgene, or whose genome has been altered by the introduction of a transgene. The term "transgenic" when used in reference to a microorganism, tissue or to a plant refers to a microorganism, tissue or plant, respectively, which comprises one or more cells that contain a transgene, or whose genome has been altered by the introduction of a transgene. Transgenic cells, microorganisms, tissues and plants may be produced by several methods including the introduction of a "transgene" comprising nucleic acid (usually DNA) into a target cell or integration of the transgene into a chromosome of a target cell by way of human intervention, such as by the methods described herein.

The term "transgene" as used herein refers to any nucleic acid sequence which is introduced into the genome of a cell by experimental manipulations. A transgene may be a "native DNA sequence," or a "heterologous DNA sequence" (i.e., "foreign DNA"). The term "native DNA sequence" refers to a nucleotide sequence which is naturally found in the cell into which it is introduced so long as it does not contain some modification (e.g., a point mutation, the presence of a selectable marker gene, etc.) relative to the naturally-occurring sequence.

The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes a native DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "transformation" as used herein refers to the introduction of a transgene into a cell. Transformation of a cell may be stable or transient.

The term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Stable transformation of a plant may also be detected by using the polymerase chain reaction to amplify transgene sequences from genomic DNA from cells of the progeny of that plant. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene.

The term "isolated" when used in relation to a nucleic acid molecule, as in "an isolated nucleic acid sequence" refers to a nucleic acid sequence that is identified and separated from at least one contaminant nucleic acid with which it is ordinarily associated in its natural source. Isolated nucleic acid is nucleic acid present in a form or setting that is different from that in which it is found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Pseudomonas, or another or related organism and thus, for example, may be an allelic or species variant of the polypeptide encoding region of the nucleic acid sequence.

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least about 20% pure, preferably at least about 40% pure, more preferably at least about 60% pure, even more preferably at least about 80% pure, and most preferably at least about 90% or 95% pure. Purity may be determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The term "identity," as known in the art, is a relationship between two or more polypeptide sequences or two or more polynucleotide sequences, as determined by a comparison of the sequences. In the art, "identity" also means the degree of sequence relatedness between polypeptide or polynucleotide sequences, as determined by the match between strings of such sequences. "Identity" can be readily calculated by known methods, including but not limited to those described in Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 994; and Sequence Analysis in Molecular Biology, von Heinje, G., Academic Press, 1987. Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403–410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403–410 (1990) and Altschul et al., Gapped BLAST and PSI-BLAST: a new generation of protein database search programs. Nucleic Acids Res. 25: 3389–3402 (1997).), ALIGN (http://dot.imgen.bcm.tmc.edu:9331/seq-search/alignment.html), and ClustalW (http://dot.imgen.bcm.edu:9331/cgi-bin/multi-align/multi-align.p1) (Higgens, 1989).

"Percentage of sequence identity" is determined by comparing two optimally aligned sequences over a comparison window, wherein the portion of the polynucleotide sequence or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. It is preferred that the comparison window is at least 50% of the coding sequence, preferably 60%, more preferably 75% or 85%, and even more preferably 95% to 100%.

The term "hybridization" as used herein includes "any process by which a strand of nucleic acid joins with a complementary strand through base pairing." [Coombs J (1994) Dictionary of Biotechnology, Stockton Press, N.Y.]. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

The phrase "hybridizes under stringent conditions" refers to the formation of a double-stranded duplex from two single-stranded nucleic acids. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid.

Nucleic acid probes to identify and clone DNA encoding polypeptides having the desired enzyme activity from strains of different genera or species can be prepared according to methods well known in the art. Such probes can be used for hybridization with the genomic or cDNA of the genus or species of interest, following standard Southern blotting procedures, in order to identify and isolate the corresponding gene therein. Both DNA and RNA probes can be used. The probes are typically labeled for detecting the corresponding gene (for example, with $^{32}P$, $^3H$, 35S, biotin, or avidin).

For long probes of at least 100 nucleotides in length, high or medium stringency conditions are used. High stringency conditions when used in reference to nucleic acid hybridization comprise conditions equivalent to binding or hybridization at 68° C. in a solution consisting of 5×SSPE, 1% SDS, 5×Denhardt's reagent and 100 $\mu$g/ml denatured salmon sperm DNA followed by washing in a solution comprising 0.1×SSPE, and 0.1% SDS at 68° C. when a probe of about 100 to about 1000 nucleotides in length is employed, or the above-mentioned conditions with 50% formamide at 42° C. High stringency washes can include 0.1×SSC to 0.2×SSC, 1% SDS, 65° C., 15–20 min. An example of stringent wash conditions for a Southern blot of such nucleic acids is a 0.2×SSC wash at 65° C. for 15 minutes (see, Sambrook et al., Molecular Cloning—A Laboratory Manual ($2^{nd}$ ed.) Vol. 1–3, Cold Spring Harbor Laboratory, Cold Spring Harbor Press, N.Y., 1989, for a description of SSC buffer). Other exemplary high stringency hybridization conditions include, for example, 7% SDS, 0.25 M sodium phosphate buffer, pH 7.0–7.2, 0.25 M sodium chloride at 65° C.–68° C. or the above-mentioned conditions with 50% formamide at 42° C. Exemplary medium stringency conditions are as described above for high stringency except that 35% formamide at 42° C. is used, and the washes are carried out at 55° C.

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the material with immobilized DNA is washed once in 6×SCC plus 0.1% SDS for 15 minutes and twice each for 15 minutes using 6×SSC at 5° C. to 10° C. below the calculated $T_m$.

A genomic DNA or cDNA library prepared from other organisms may be screened for DNA which hybridizes with the probes described above and which encodes a polypeptide having the desired enzyme activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable material. In order to identify a clone or DNA which is homologous with a selected sequence or a subsequence thereof, the material with immobilized DNA is used in a Southern blot. For purposes of the present invention, hybridization indicates that the nucleic acid sequence hybridizes to a labeled nucleic acid probe corresponding to the selected nucleic acid sequence, its complementary strand, or a subsequence thereof, under medium to high stringency conditions. Molecules to which the nucleic acid probe hybridizes under these conditions are detected using X-ray film.

The term "nucleic acid construct" refers to a nucleic acid molecule, either single- or double-stranded, which is isolated from a naturally occurring gene or which has been modified to contain segments of nucleic acid which are combined and juxtaposed in a manner which would not otherwise exist in nature. The nucleic acid construct can include, for example, a coding sequence of the invention, and control sequences such as a promoter, and transcriptional and translation stop signals. The term nucleic acid construct is synonymous with the term expression cassette when the nucleic acid construct contains all the control sequences required for expression of a coding sequence of the present invention. Exemplary constructs include plasmids and vectors, including cloning vectors, recombinant expression vectors. A "vector" is a nucleic acid composition which can transduce, transform or infect a cell and generally be replicated in the cell, thereby causing the cell to express vector-encoded nucleic acids and, optionally, proteins other than those native to the cell, or in a manner not native to the cell. A vector includes a nucleic acid (ordinarily RNA or DNA) to be expressed by the cell. A vector optionally includes materials to aid in achieving entry of the nucleic acid into the cell, such as a retroviral particle, liposome, protein coating or the like. Vectors contain nucleic acid sequences which allow their propagation and selection in bacteria or other non-plant organisms. For a description of vectors and molecular biology techniques, see Current Protocols in Molecular Biology, Ausubel, et at., (eds.), Current Protocols, a joint venture between Greene Publishing Associates, Inc. and John Wiley & Sons, Inc., (through and including the 1998 Supplement) (Ausubel).

The term "coding sequence" is defined herein as a nucleic acid sequence which directly specifies the amino acid sequence of its protein product, e.g., a sequence which is transcribed into mRNA and translated into a polypeptide. The boundaries of the coding sequence are generally determined by the ATG start codon (eukaryotes) and a translation terminator (stop codon). A coding sequence can include, but is not limited to, DNA, cDNA, and recombinant nucleic acid sequences.

The term "sense orientation" refers to the orientation of a cDNA sequence or coding sequence with respect to the promoter in a construct, such that the 5' end of the cDNA sequence or coding sequence is adjoined to the promoter.

The term "control sequences" is defined to include all components which are necessary or advantageous for the expression of a polypeptide. Such control sequences include, but are not limited to, a leader, a polypeptide sequence, a promoter, a signal peptide sequence or a targeting sequence, an enhancer, and a transcription terminator. At a minimum, the control sequences include a promoter, and a transcriptional terminator sequence. The portion of a gene or nucleic acid construct containing the 5' leader sequence, generally 5 to 15 nucleotides in length immediately upstream of the ATG start codon, can also be considered a control sequence as it can affect the efficiency of translation. The control sequences may be provided with linkers for the purpose of introducing specific restriction sites facilitating ligation of the control sequences with the coding region of the nucleic acid sequence encoding a polypeptide. The term "operably linked" is defined here as a configuration in which a control sequence is placed at a position relative to the coding sequence of the nucleic acid sequence such that the control sequence directs the production of a messenger RNA and/or a polypeptide.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription. A DNA sequence is "operatively associated" with the promoter in a cell when RNA polymerase which binds the promoter sequence transcribes the coding sequence into mRNA which is then in turn translated into the protein encoded by the coding sequence.

The control sequence may also be a suitable transcription terminator sequence, a sequence recognized by a host cell to terminate transcription. The terminator sequence is operably linked to the 3' terminus of the nucleic acid sequence encoding the polypeptide.

The control sequence may also be a suitable leader sequence, a nontranslated region of an mRNA which is important for translation by the host cell. The leader sequence is operably linked to the 5' terminus of the nucleic acid sequence encoding the polypeptide.

The control sequence may also be a polyadenylation sequence, a sequence operably linked to the 3' terminus of the nucleic acid sequence and which, when transcribed, is recognized by the host cell as a signal to add polyadenosine residues to transcribed mRNA.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5$\propto$ end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide.

The control sequence may also be a localization peptide that codes for an amino acid sequence linked to the carboxy terminus of a polypeptide and directs the encoded polypeptide to specific locations in a cell.

The term "expression vector" refers to a vector comprising a nucleic acid construct and sequences for delivery into and autonomous replication in microbial host cells. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, subcellular localization or the like. The variant sequence may be constructed on the basis of the nucleic acid sequence presented as the polypeptide encoding part of an exemplified sequence, a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for enzyme activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The term "host cell" is a cell which has been transformed or transfected, or is capable of transformation or transfection by an exogenous polynucleotide sequence. The host cell may be a unicellular microorganism, e.g., a prokaryote, or a non-unicellular microorganism, e.g., a eukaryote. Eukaryote cells can include any cell such as from an insect, microorganism, fungus or plant. Exemplary host cells, introduction of a vector into a host cell, and cloning are described in U.S. Pat. No. 5,374,540 which is hereby incorporated by reference.

Microorganism host cells include but are not limited to members of the kingdom Prokaryotae.

Plant host cells include but are not limited to, somatic cells, gametes or embryos. "Embryo" refers to a sporophytic plant before the start of germination. Embryos can be formed by fertilization of gametes by sexual crossing or by selfing. A "sexual cross" is pollination of one plant by another. "Selfing" is the production of seed by self-pollenization, i.e., pollen and ovule are from the same plant. The term "backcrossing" refers to crossing a $F_1$ hybrid plant to one of its parents. Typically, backcrossing is used to transfer genes which confer a simply inherited, highly heritable trait into an inbred line. The inbred line is termed the recurrent parent. The source of the desired trait is the donor parent. After the donor and the recurrent parents have been sexually crossed, $F_1$ hybrid plants which possess the desired trait of the donor parent are selected and repeatedly crossed (i.e., backcrossed) to the recurrent parent or inbred line.

Embryos can also be formed by "embryo somatogenesis" and "cloning." Somatic embryogenesis is the direct or indirect production of embryos from cells, tissues and organs of plants. Indirect somatic embryogenesis is characterized by growth of a callus and the formation of embryos on the surface of the callus. Direct somatic embryogenesis is the formation of an asexual embryo from a single cell or group of cells on an explant tissue without an intervening callus phase. Because abnormal plants tend to be derived from a callus, direct somatic embryogenesis is preferred.

The term "plant" as used herein refers to a plurality of plant cells which are largely differentiated into a structure that is present at any stage of a plant's development. Such structures include, but are not limited to, whole plants, plant parts or organs, e.g., callus, root, fruit, seed, shoot, stem, tuber, leaf, and floret organs, and progeny of same. Plant progeny includes progeny of plants, plant parts and plant cells. The class of plants which can be used in the methods of the invention is generally as broad as the class of higher plants amenable to transformation techniques, including both monocotyledonous (a monocot) and dicotyledonous (a dicot) plants.

The term "progeny" refers to the descendants of a particular plant or regenerant (self-cross) or pair of plants (crossed or backcrossed). The descendants by self-fertilization can be of the $T_1$, the $T_2$, or any subsequent generation, and descendants by crossing can be of the $F_1$, the $F_2$, or any subsequent generation. Typically, the parents are the pollen donor and the ovule donor which are crossed to make the progeny plant of this invention. Parents also refer to $F_1$ parents of a hybrid plant of this invention (the $F_2$ plants). Finally, parents refer to a recurrent parent which is backcrossed to hybrid plants of this invention to produce another hybrid plant of this invention.

The term "plant tissue" includes differentiated and undifferentiated tissues of plants including, but not limited to, roots, shoots, leaves, pollen, seeds, tumor tissue and various types of cells in culture (e.g., single cells, protoplasts, embryos, callus, etc.). Plant tissue may be in planta, in organ culture, tissue culture, or cell culture.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

"Transgenic plants" are plants into which a nucleic acid sequence has been introduced through recombinant techniques, i.e., nucleic acid-containing vectors, cloning, somatic embryogenesis or any other technique used by those of skill to produce plants.

"Line" pertains to a plant or its germplasm, a primary regenerant from transformation, ($T_o$) plant or its progeny, resulting from genetic transformation, in which all or a portion of transgene has been stably integrated.

The term "monocot" refers to a plant species having a single cotyledon, including wheat, oat, barley, rice, rye, triticale, maize (corn), and other cereals, as well as sugarcane, sorghum, pineapple, yam, onion, banana, coconut, date, hops, and grasses such as turf grass, meadow grass and forage grass.

Dicotyledonous refers to plant species characterized by a pair of embryonic seed leaves that appear at germination, including tobacco, potato, tomato, soybean, pea, bean, sugar beet, papaya, Cucurbita (squash, cucumber, melon, pumpkin, zucchini), stone fruit trees, cotton, sweet potato, cruciferous plants (family Brassicaceae), such as cauliflower, rape seed, and the closely related model organism *Arabidopsis thaliana*.

Other plants susceptible to fungal or bacterial diseases are also encompassed.

DETAILED DESCRIPTION OF THE INVENTION

I: PhzO Enzyme and Nucleic Acid Molecules Encoding Polypeptides Having PhzO Activity The present invention is directed to phzO nucleic acid sequences which encode polypeptides having PhzO activity and isolated polypeptides having PhzO activity.

A. Nucleic Acid Molecules which Encode Polypeptides Having PhzO Activity

PhzO refers to a polypeptide having the ability to convert phenazine-1-carboxylic acid to at least one 2-hydroxylated phenazine. In a first embodiment, the present invention is directed to an isolated nucleic acid molecule encoding a polypeptide having PhzO activity selected from the group consisting of:

(a) a nucleotide sequence as given in SEQ ID NO:1 from nucleotide 76 to nucleotide 1564 or from nucleotide 89 to nucleotide 1564;

(b) a nucleotide sequence encoding a polypeptide having PhzO activity comprising an amino acid sequence of SEQ ID NO:2;

(c) a nucleic acid sequence having at least 50% nucleotide sequence identity with SEQ ID NO:1 from nucleotide 89 through nucleotide 1564 and wherein said nucleic acid sequence encodes a polypeptide having PhzO activity;

(d) a nucleic acid sequence encoding a polypeptide having an amino acid sequence which has at least 60% sequence identity with SEQ ID NO:2 and wherein said encoded polypeptide has PhzO activity;

(e) a nucleic acid sequence which hybridizes under medium or high stringency conditions with the nucleotide sequence of SEQ ID NO:1 from nucleotide 89 through nucleotide 1564 and wherein said DNA sequence encodes a polypeptide having PhzO activity;

(f) a subsequence of (a)–(e) wherein the subsequence encodes a polypeptide fragment which has PhzO activity.

A specific embodiment of a phzO nucleotide sequence is given in SEQ ID NO:1. This DNA sequence is 2869 bp in length. The open reading frame (coding portion), initiating at base 89 and terminating at base 1564 encodes a protein 491 amino acids in length (SEQ ID NO:2). The PhzO gene is from nucleotide 76 to1564; the RBS is from nucleotide 76 to 81.

Figure 3:
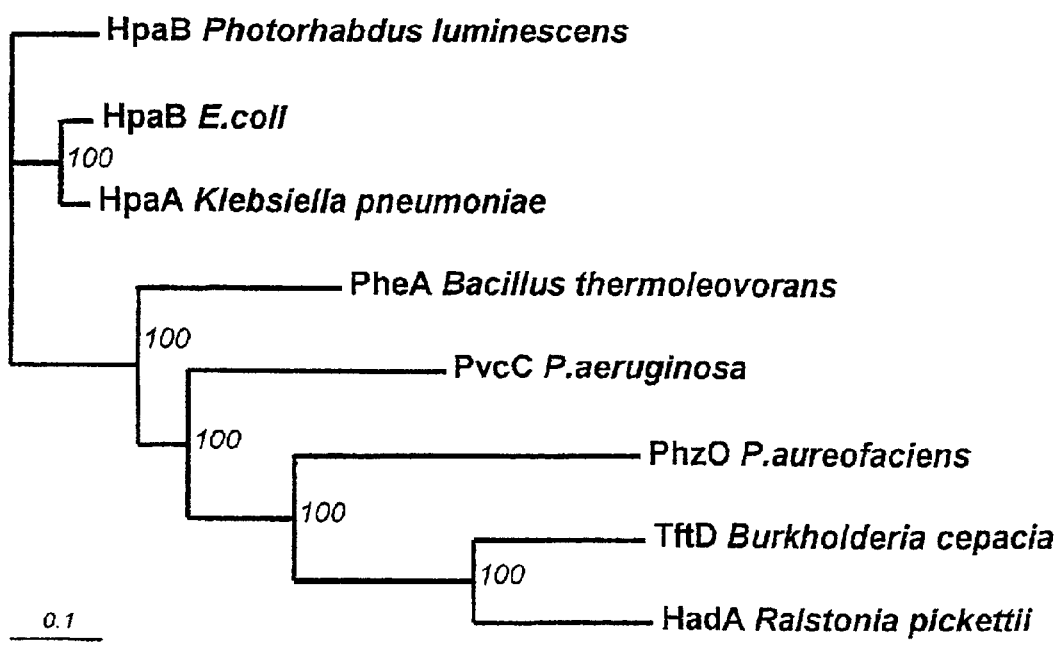
FIG. 3 shows the phylogenetic relationship between PhzO and various bacterial aromatic monooxygenases. The neighbor-joining tree with bootstrap support was constructed and visualized by using the CLUSTAL W and TreeView 1.5.0 programs, respectively (R. D. M. Page, *Computer Applications in the Biosciences* 12:357–358, 1996).

The novel gene phzO was obtained from the source organism *Pseudomonas aureofaciens* 30–84, and was located 271 nucleotides downstream from phzD, in the core phenazine operon phzXYFABCD of *P. aureofaciens* 30–84, and was preceded by a well-conserved potential ribosome binding site, GAGG. phzO encoded a 491-amino acid PhzO polypeptide with a calculated molecular mass of 55.1 kDa. The PhzO is a aromatic monooxygenase responsible for the hydroxylation of phenazine-1-carboxylic acid to produce 2-hydroxyphenazine-1-carboxylic acid. Homology searches with the deduced amino acid sequence revealed similarity to bacterial aromatic hydroxylases and monooxygenases (Table 3). Phylogenetic analysis of these aligned protein sequences resulted in the tree shown in FIG. 3. The high bootstrap values (from 1,000 resamplings) showed the robustness of these groups.

As shown in detail, below, results of our study show clearly that phzXYFABCD, the core phenazine biosynthetic operon of strain 30–84, is responsible only for the synthesis of phenazine-1-carboxylic acid. When transformed with these genes, the sole phenazine product synthesized by *P. fluorescens* strains Q8r1-96 and M4-80R (which themselves do not produce phenazines) was PCA. However, phenazine-non-producing strains transformed with phzXYFABCD and phzO, or *P. fluorescens* 2–79 transformed with phzO, synthesized hydroxyphenazine compounds in addition to PCA, and *E. coli* expressing phzO rapidly converted exogenously-supplied PCA to 2-hydroxylated phenazine products. Finally, a mutant of 30–84 inactivated in phzO produced only PCA.

In another embodiment, the nucleic acid molecule is the sequence contained in plasmid pUCP2.9XP or plasmid pGEM-PHZO (Table 1).

Statement of Deposit

Plasmids identified below were introduced into the designated host strains and the transformed strains were deposited under terms of the Budapest Treaty with Agricultural Research Service Culture Collection (NRRL) National Center for Agricultural Utilization Research, Agricultural Research Service, U.S. Department of Agriculture, 1815 North University Street, Peoria, Ill. 61604 USA on the date listed and given the following accession numbers:

| Host | Plasmid | Accession No. | Date of Deposit |
| --- | --- | --- | --- |
| *E. coli* JM109 | pUC2.9XP, clone 12 | NRRL B-30341 | Oct. 06, 2000 |
| *E. coli* JM109 | pUC2.9XP, clone 16 | NRRL B-30342 | Oct. 06, 2000 |
| *P. fluorescens* 2-79 | pUC2.9XP, clone 12 | NRRL B-30343 | Oct. 06, 2000 |
| *P. fluorescens* 2-79 | pUC2.9XP, clone 12 | NRRL B-30344 | Oct. 06, 2000 |
| *E. coli* JM109 | pGEM-PHZO | NRRL B-30345 | Oct. 11, 2000 |
| *E. coli* JM109 | pGEM-PHZO | NRRL B-30346 | Oct. 11, 2000 |

The invention also encompasses nucleic acid sequences which have a degree of sequence identity to the coding region of SEQ ID NO:1 of at least 50%, preferably at least about 60%, more preferably at least about 70%, even more preferably at least about 80 or 85%, more preferably at least about 90%, and even more preferably about 95–100% and which encode a polypeptide which has the ability to convert phenazine-1-carboxylic acid to a 2-hydroxylated phenazine. For purposes of the present invention, the degree of identity between two nucleic acid sequences is determined by the GCG program package (Devereux, J., et al., *Nucleic Acids Research* 12(1): 387 (1984)).

Further, nucleic acid sequences which hybridize under medium stringency or high stringency conditions, as defined above, with the coding region of the DNA sequence of SEQ ID NO:1 and which encode a polypeptide which has the ability to synthesize a 2-hydroxylated phenazine from phenazine-1-carboxylic acid are included in the present invention.

Also encompassed by the invention are subsequences of at least 100 contiguous nucleotides and preferably at least 200 contiguous nucleotides which hybridize under medium stringency or high stringency conditions, as defined above, with the coding region of the DNA sequence of SEQ ID NO:1.

The invention further encompasses a complementary strand of a nucleic acid sequence or subsequence of at least 100 contiguous nucleotides and preferably at least 200 contiguous nucleotides of a nucleic acid sequence which hybridizes under medium stringency or high stringency conditions, as defined above, with the coding region of the DNA sequence of SEQ ID NO:1.

The invention is further directed to a subsequence of the aforenamed nucleic acid sequences wherein the subsequence encodes a polypeptide fragment which has phzO activity.

B. Polypeptides Having PhzO Activity

The present invention is also directed to isolated polypeptides having PhzO activity, e.g., the ability to convert phenazine-1-carboxylic acid to a 2-hydroxylated phenazine, which are encoded by the nucleic acid molecules described above. Isolated polypeptides having PhzO activity comprise:

(a) a polypeptide having an amino acid sequence of SEQ ID NO:2;

(b) a polypeptide having an amino acid sequence which has at least 60% identity with amino acids 1 to 491 of SEQ ID NO:2;

(c) a polypeptide encoded by a nucleic acid sequence which hybridizes under medium stringency or high stringency conditions with (i) SEQ ID NO:1 from nucleotide 89 through nucleotide 1564; (ii) a subsequence of (i) of at least 100 nucleotides, or (iii) a complementary strand of (i) or (ii); and (d) a fragment of (a)–(c) that has the ability to convert phenazine-1-carboxylic acid to a 2-hydroxylated phenazine.

An isolated PhzO polypeptide is specifically exemplified in SEQ ID NO:2. Homology searches with the deduced amino acid sequence revealed similarity to bacterial aromatic hydroxylases and monooxygenases (Table 3). Phylogenetic analysis of these aligned protein sequences resulted in the tree shown in FIG. 3. The high bootstrap values (from 1,000 resamplings) showed the robustness of these groups.

Isolated nucleic acid sequences encoding polypeptides comprising an amino acid sequence which has a degree of identity to the amino acid sequence of SEQ ID NO:2 with amino acids 1 to 491 of at least about 60%, preferably at least 70%, more preferably at least about 80%, further more preferably at least about 85%, even more preferably at least about 95% or 100%, and which have the ability to convert phenazine-1-carboxylic acid to a 2-hydroxylated phenazine (homologous polypeptides), are encompassed by the invention. For purposes of the present invention, the degree of identity between two amino acids is determined by the method of Pearson (*Methods Enzymology* 183:63–98, 1990).

The polypeptides of the present invention may comprise amino acids 1 to 491 of SEQ ID NO:2 or a fragment thereof that has the ability to convert phenazine-1-carboxylic acid to a 2-hydroxylated phenazine.

A fragment of SEQ ID NO:2 is a polypeptide having one or more amino acids deleted from the amino and/or carboxyl terminus of this amino acid sequence. Preferably, a fragment contains at least 417 amino acid residues, more preferably at least 442 amino acid residues, and most preferably at least 466 amino acid residues.

The present invention relates to isolated polypeptides having PhzO activity which are encoded by nucleic acid sequences which hybridize under medium stringency conditions or high stringency conditions, as described in detail above, with (i) SEQ ID NO:1 from nucleotide 89 through nucleotide 1564; (ii) a subsequence of (i) of at least 100 nucleotides, or (iii) a complementary strand of (i) or (ii). The subsequence of SEQ ID NO:1 may be at least 100 contiguous nucleotides or preferably at least 200 contiguous nucleotides. Moreover, the subsequence may encode a polypeptide fragment which has the ability to convert phenazine-1-carboxylic acid to a 2-hydroxylated phenazine.

The degeneracy of the genetic code is well known to the art; therefore, synonymous coding sequences with one or more codon substitutions can be readily determined by one of ordinary skill in the art. Synonymous coding sequences vary from the exemplified coding sequences but encode proteins of the same amino acid sequences as those specifically provided herein.

Examples of conservative substitutions are within the groups of basic amino acids (such as arginine, lysine and histidine), acidic amino acids (such as glutamic acid and aspartic acid), polar amino acids (such as glutamine and asparagine), hydrophobic amino acids (such as leucine isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art as described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

The polypeptides of the present invention have at least 20%, preferably at least 40%, more preferably at least 60%, even more preferably at least 80%, even more preferably at least 90%, and most preferably at least 100% of the PhzO activity of the polypeptide of SEQ ID NO:2.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. Exemplary microorganisms are members of the genera Escherichia, Pseudomonas, Streptomyces, Nocardia, Sorangium, Brevibacterium, and Burkholderia.

A polypeptide of the present invention may be a bacterial polypeptide. For example, the polypeptide may be a gram positive bacterial polypeptide such as a Bacillus polypeptide, e.g., a *Bacillus brevis, Bacillus circulans, Bacillus licheniformis, Bacillus megaterium, Bacillus subtilis*, or *Bacillus thuringiensis* polypeptide; or a Streptomyces polypeptide, e.g., a *Streptomyces lividans* or *Streptomyces murinus* polypeptide; or a gram, negative bacterial polypeptide, e.g., an *E. coli* or a Pseudomonas sp. polypeptide, e.g., *Pseudomonas fluorescens, Pseudomonas chlororaphis, Pseudomonas putida, Pseudomonas aeruginosa*, or *Pseudomonas aurantiaca*. Exemplary Pseudomonas sp. include *P. fluorescens* 2–79, *P. fluorescens* Q8r1-96 (NRRL B-21806), and *P. fluorescens* Z30–97 (NRRL B-21908).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-PhzO polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

C. Comparison to Known Hydroxylases

Results of computer analyses indicated that phzO encodes for a 55-kDa protein with similarity to bacterial aromatic monooxygenases. That PhzO belongs to a recently-defined (Galán et al., *J. Bacteriol.* 182:627–636, 2000) family of two-component nonheme flavin-diffusible (TC-FDM) bacterial aromatic monooxygenases is supported by results of both pairwise (high Z-scores) and multiple sequence alignments (high bootstrap values). These enzymes are NAD(P)H-dependent flavoproteins that lack the defined GXGXXG FAD/NADH binding site typical of aromatic monooxygenases. Instead, they function in concert with a reductase component that uses NAD(P)H to generate a reduced flavin. The flavin then diffuses to the oxygenase, where it serves as a cosubstrate in the oxidation of aromatic compounds by molecular oxygen (Galán et al., 2000, supra; Xun and Sandvik, *Appl. Environ. Microbiol.* 66:481–486). TC-FDM monooxygenases hydroxylate aromatic substrates in either the ortho or the para position, and include both dehalogenating (HadA from *Ralstonia pickettii*, PheA from *Bacillus thermoleovorans*, and TfD from *Burkholderia cepacia*), and nondehalogenating (HpaB from *E. coli*, HpaB from *Photorhabdus luminescens*, HpaA from *Klebsiella pneumoniae*, PvcC from *P. aeruginosa*) enzymes (Dufffer and Müller, *FEMS Microbiol. Lett.* 161:37–45, 1998; Gibello et al., *Arch. Microbiol.* 167:160–166, 1997, Hübner et al., *Appl. Environ. Microbiol.* 64:2086–2093, 1998; Prieto and Garcia *J. Biol. Chem.* 269:22823–22829, 1994; Stintzi et al., *J. Bacteriol.* 181:4118–4124, 1999; Takizawa et al., *J. Ferment. Bioeng.* 80:318–327, 1995). Many require the presence of an additional 19- to 21-kDa "coupling" subunit (Gibello et al., 1997, supra; Hübner et al., 1998, supra; Prieto and Garcia, 1994, supra; Takizawa et al., 1995, supra) to provide reduced flavin, but at least for HpaB, the archetype of this family, this requirement can be satisfied with FADH2 provided exogenously or generated by an alternative flavin reductase (Galán et al., 2000, supra; Xun and Sandvik, 2000, supra). This apparently also is the case for PhzO, since the cloned gene in either pUCP2.9XP or pGEM-PHZO (which contained very little flanking sequence from *P. aureofaciens* 30–84) was sufficient to catalyze the conversion of PCA to 2-hydroxyphenazines in *E. coli*. Whereas the genes encoding the oxidase and reductase components of most known TC-FDM enzymes are situated near one other on the chromosome (Galán et al., 2000, supra), we found no detectable similarity with known flavin reductases in the 1.3 kb DNA segment downstream of phzO. Although a functionally "dedicated" reductase may be encoded elsewhere in the genome of strain 30–84, such an enzyme clearly is not required for phenazine 2-hydroxylation in *E. coli*. The apparent absence of a linked reductase gene and the relatively low level of overall homology between PhzO and other members of the TC-FDM family distinguish this phenazine-modifying enzyme from other oxygenases.

Figure 4:
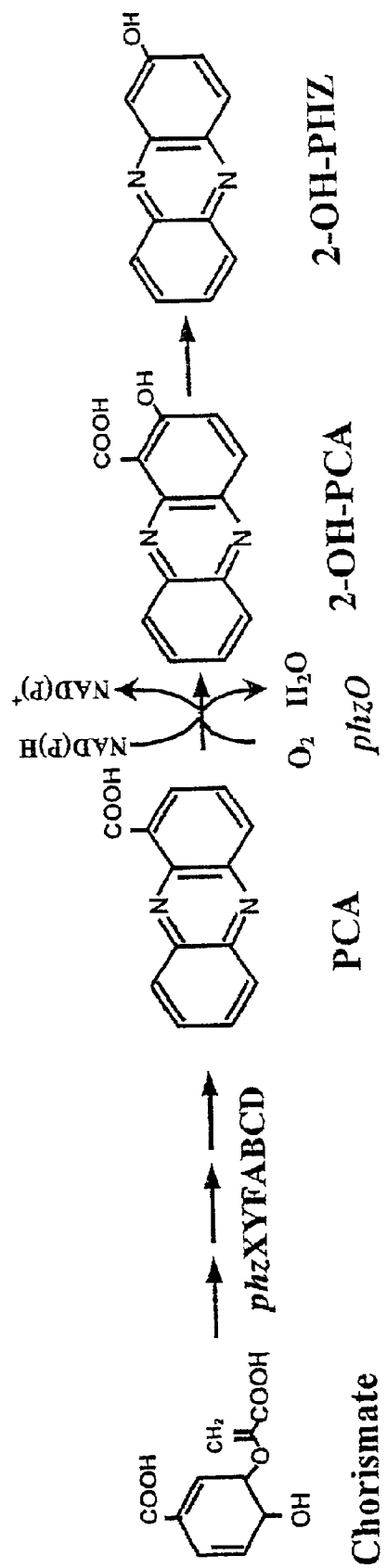
FIG. 4 shows the proposed mechanism for the production of 2-hydroxyphenazine-1-carboxylic acid and 2-hydroxyphenazine in *P. aureofaciens* 30–84.

Earlier, Flood et at. (*J. C. S. Perkins Transactions* 1:622–627, 1972) in a study with deuteriated precursors revealed that hydroxylated phenazines are synthesized in *P. aureofaciens* through the formation of a hypothetical arene intermediate in the order: PCA→2-OH-PCA→2-OH-PHZ (Flood et al., supra). The authors also concluded that the hydroxylation of PCA occurred inefficiently, since PCA was more abundant in the extracts than the hydroxylated derivatives. Based on the results of our study, we speculate that 2-hydroxylation of PCA is carried out in *P. aureofaciens* by a nonheme, flavin-diffusible monooxygenase, PhzO, which adds a hydroxyl group to PCA at the ortho position relative to the carboxyl group, resulting in the synthesis 2-OH-PCA (FIG. 4). The reaction presumably also requires a yet-unidentified, highly active reductase, NAD(P)H, flavin, and O2. As speculated previously (14), the subsequent decarboxylation of 2-OH-PCA to 2-OH-PHZ occurs spontaneously in the absence of enzymes. Up to 74% of 2-OH-PCA in phosphate buffer at pH 7 was converted to 2-OH-PHZ after 18 hours, whereas lesser amounts (33% and 62%) were converted in buffers at pH values of 6 and 8, respectively (G. Phillips and L. S. Thomashow, unpublished data).

II. Using Probes to Identify and Isolate Homologs of the Sequences

The isolation of homolog genes may be accomplished by a number of techniques. For instance, nucleic acid probes based on the disclosed sequences can be used to isolate the desired gene from a cDNA or genomic DNA library, as described in detail, above. Nucleic acid probes can be either DNA or RNA. The desired gene can be isolated by hybridization of the probes to target sequences, including genomic library clones, cDNA library clones, or uncloned isolated DNA or cDNA fragments. Hybridization can be carried out under stringent, highly stringent, or low-stringency conditions either on membranes or in solution. Nucleic acid probes can be used as restriction fragment length polymorphic (RFLP) markers for the genetic mapping of loci for the identification of homologous genes or loci.

III. Using Primers to Amplify Nucleotide Sequences

Primers based on the disclosed sequences can be used to isolate the desired genes from a cDNA or genomic library. The nucleic acids of interest can be amplified from nucleic acid samples using amplification techniques. For instance, polymerase chain reaction (PCR) technology can be used to amplify the sequences directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired DNA or mRNA in samples, for nucleic acid sequencing, or for other purposes. For a general overview of PCR see, PCR Protocols: A Guide to Methods and Applications, Innis, et al. (eds.), Academic Press, San Diego (1990).

IV. Preparation of Recombinant Nucleic Acid Molecules (Constructs)

In one embodiment of this invention, recombinant nucleic acid molecules which contain isolated nucleic acid sequences which encode a polypeptide having PhzO activity and are suitable for transformation of host cells are prepared. A nucleic acid sequence coding for the desired polypeptide, for example, a cDNA or a genomic sequence encoding a full length protein or, a nucleic acid sequence encoding a homologous polypeptide is conveniently used to construct a recombinant expression cassette which can be introduced into the desired host cell. An expression cassette will typically comprise the nucleic acid sequence operably linked to a one or more control sequences which direct the expression of the coding sequence in a suitable host cell under conditions compatible with the control sequences, and may include other transcriptional and translational initiation regulatory sequences which will direct the transcription of the sequence in the intended tissues of the transformed host cell. Expression will be understood to include any step involved in the production of the polypeptide including, but not limited to, transcription, post-transcriptional modification, translation, post-translational modification, and secretion.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequences include all components which are necessary or advantageous for the expression of a polypeptide of the present invention. Such control sequences include, but are not limited to, a leader, polyadenylation sequence, propeptide sequence, promoter, signal peptide sequence, and transcription terminator sequence, as described in detail above.

Promoter sequence as used herein, refers to a DNA sequence which when ligated to a nucleotide sequence of interest is capable of controlling the transcription of the nucleotide sequence of interest into mRNA. This is discussed in detail, above.

Promoters may be constitutive. The term "constitutive" when made in reference to a promoter means that the promoter is capable of directing transcription of an operably linked nucleic acid sequence under most environmental and developmental conditions in the absence of a stimulus (e.g., heat shock, chemicals, light, etc.), and/or in several or many tissues, cell types, or organs.

Promoters may be tissue specific or cell specific. The term "tissue specific" as it applies to a promoter refers to a promoter that is capable of directing selective expression of a nucleotide sequence of interest to a specific type of tissue in the relative absence of expression of the same nucleotide sequence of interest in a different type of tissue. Tissue specificity of a promoter may be evaluated by, for example, operably linking a reporter gene to the promoter sequence to generate a reporter construct, introducing the reporter construct into the genome of a microorganism or plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic microorganism or plant.

Techniques are well known in the art for expression of genes involved in the biosynthesis of antibiotic compounds in gram-negative and gram-positive bacteria and fungi. Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful Proteins from Recombinant Bacteria" in *Scientific American*, 1980, 242: 74–94; and in Sambrook et al., 1989, supra.

Techniques for expression of expression of genes involved in the biosynthesis of antibiotic compounds in plants are known. A constitutive plant promoter fragment may be employed which will direct expression of the PhzO enzyme in some to many tissues of a plant. Such promoters are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefuciens*, and other transcription initiation regions from various plant genes known to those of skill in the art.

Promoters for constitutive expression of genes in cereals include: maize ubiquitin-1, young leaf, root, pollen, seed (cereals) (Christensen and Quail, *Trans. Res.* 5:213–218 1996); maize Adh-1, embryo shoots, roots, anther, pollen, seed (rice) (Freeling and Bennett, *Annual Rev. Genet.* 19:297–323, 1985); rice ACT-1, shoot leaf, root, floral parts, including pollen (rice) (Zhang et al., *Plant Cell* 3: 1155–1165,1991); CaMV 35S, leaf, root (rice) (Battraw et al., *Plant Mol. Biol.* 15: 527–538,1990); ScBv, stem, palea, lemma, other floret organs, anther (oat) (Tzafri et al., Plant Mol Biol 38: 347–356, 1998).

Organ-specific promoters may be, for example, a promoter from storage sink tissues such as seeds, potato tubers, and fruits (Edwards & Coruzzi, 1990, *Ann. Rev. Genet.* 24:275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39:885–889), the storage protein napA promoter from *Brassica napus*, or any other seed specific promoter known in the art. Furthermore, the promoter may be a leaf specific promoter such as the rbcS promoter from rice or tomato (Kyozuka et al., 1993, *Plant Physiology* 102:991–1000, or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22:573–588).

Alternatively, the plant promoter may be under environmental or developmental control. Such promoters are referred to here as "inducible" promoters. Examples of environmental conditions that may effect transcription by inducible promoters include pathogen attack, anaerobic conditions, or the presence of light.

A promoter enhancer element may also be used to achieve higher expression of the gene in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin gene to enhance expression.

A preferred category of promoters is that which is wound inducible. Numerous promoters have been described which are expressed at wound sites and also at the sites of phytopathogen infection. These are suitable for the expression of phzO genes because phenazine biosynthesis is turned on by phytopathogen infection, and thus the phenazine compound only accumulates when infection occurs. Ideally, such a promoter should only be active locally at the sites of infection, and in this way phenazine compounds only accumulate in cells which need to synthesize them to kill the invading phytopathogen. Preferred promoters of this kind include those described by Stanford et al., *Mol. Gem Genet.* 215: 200–208 (1989), Xu et al., *Plant Molec. Biol.* 22: 573–588 (1993), Logemann et al., *Plant Cell* 1: 151–158 (1989), Rohrmeier & Lehle, *Plant Molec. Biol.* 22: 783–792 (1993), Firek et al., *Plant Molec. Biol.* 22: 129–142 (1993) and Warner et al., *Plant J.* 3: 191–201 (1993).

V. Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is fully or partially integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vector may also contain sequences that stabilize the integration and expression of the nucleic acid construct in a host cell. These include DNA sequences carrying matrix attachment regions.

The vector may also contain one or more selectable markers which permit easy selection of transformed cells.

The vector may also contain an element(s) that permits integration of the vector into the host cell's genome or autonomous replication of the vector in the cell independent of the genome.

For integration into the host cell genome, the vector may rely on the nucleic acid sequence encoding the polypeptide or any other element of the vector for integration of the vector into the genome by homologous or nonhomologous recombination.

For autonomous replication, the vector may further comprise an origin of replication enabling the vector to replicate autonomously in the host cell in question.

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

VI. Preparation of Transgenic Host Cells and Production of Polypeptide

The present invention also relates to recombinant host cells, comprising a nucleic acid sequence of the invention, which are advantageously used in the recombinant production of the polypeptides. Preparation of transformed host cells and cloning methods are described by U.S. Pat. No. 5,374,540, which is incorporated herein by reference.

The host cell may be a unicellular microorganism, e.g., a prokaryote, or a non-unicellular microorganism, e.g., a eukaryote. Eukaryote cells can include any cell such as from an insect, fungus or plant. The term "plant" includes whole plants, plant parts or organs, plant tissue, as described in detail, above.

The invention includes methods for producing a polypeptide having PhzO activity in a recombinant host, comprising the steps of transforming a host with one or more nucleic acid molecules that encode a polypeptide having PhzO activity and growing the host under conditions which allow biosynthesis of PhzO in the host.

The present invention also relates to methods for producing a polypeptide comprising cultivating a host cell under conditions suitable for production of the polypeptide and recovering the polypeptide. The cells are cultivated in nutrient medium suitable for production of the polypeptide using methods know in the art. The polypeptides may be detected and recovered using methods known in the art.

The present invention also relates to methods for producing a polypeptide of the present invention comprising (a) cultivating a transgenic microorganism or a microorganism cell comprising a nucleic acid sequence encoding a polypeptide having enzyme activity of the present invention under conditions conducive for production of the polypeptide; and (b) recovering the polypeptide.

The present invention also relates to methods for producing a polypeptide of the present invention comprising (a) cultivating a transgenic plant or a plant cell comprising a nucleic acid sequence encoding a polypeptide having enzyme activity of the present invention under conditions conducive for production of the polypeptide; and (b) recovering the polypeptide.

The polypeptides may be detected using methods known in the art that are specific for the polypeptides. These detection methods may include use of specific antibodies, formation of an enzyme product, or disappearance of an enzyme substrate. Alternatively HPLC and mass spectrometry may be used to determine activity of the polypeptide.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

VII. Preparation of Transgenic Microorganisms

The transgenic microorganism or microorganism cell expressing an RNA transcript or polypeptide of the present invention may be constructed in accordance with methods known in the art. In brief, the microorganism or microorganism cell is constructed by incorporating one or more expression constructs encoding a polypeptide of the present invention into the host and propagating the resulting modified microorganism or microorganism cell.

Preparation of transgenic *E. coli* and *Pseudomonas fluorescens* 2–79, *Pseudomonas fluorescens* Q8r1-96, and *P. aureofaciens* 30–84 are described in detail, below. Transformation of microorganism with genes encoding a polypeptides for biosynthesis of an antibiotic are also described in U.S. Pat. Nos. 6,051,383; 5,955,298; 5,817,502; 5,756,087; 5,723,759; 5,716,849; 5,698,425; 5,679,560; and 5,662,898; U.S. patent application Ser. No. 08/994,035, and journal publications Mavrodi et al., 1998, supra; and Pierson et al., 1995, supra.

In a preferred embodiment of this invention, the transgenic microorganisms of this invention are members of the genera Escherichia, Enterobacter, Klebsiella, Rhizobium, Serratia, Pseudomonas, Streptomyces, Nocardia, and Brevibacterium. In a more preferred embodiment, the transgenic microorganisms are *Pseudomonas fluorescens, P. aureofaciens, P. putida, P. chlororaphis, P. aeruginosa*, and *P. aurantiaca*.

Microorganisms which are suitable for the heterologous overexpression of phzO genes are all microorganisms which are capable of colonizing plants or the rhizosphere. As such they will be brought into contact with phytopathogenic fungi, bacteria and nematodes causing an inhibition of their growth. These include gram-negative microorganisms such as Pseudomonas, Enterobacter and Serratia, the gram-positive microorganism Bacillus and the fungi Trichoderma and Gliocadium.

Expression in heterologous biocontrol strains requires the selection of vectors appropriate for replication in the chosen host and a suitable choice of promoter. Techniques are well known in the art for expression in gram-negative and gram-positive bacteria and fungi and are described elsewhere in this specification.

In one aspect of the invention, a non-phenazine producing microorganism strain is transformed with an operon capable of producing phenazine-1-carboxylic acid, and a nucleic acid sequence which encodes for a polypeptide having PhzO activity, to thereby obtain transformed strains which produce 2-hydroxylated phenazine.

In another aspect of the invention, microorganism strains which contain a nucleic acid sequence which encodes for a polypeptide having PhzO activity are fed phenazine-1-carboxylic acid to produce 2-hydroxylated phenazines.

VIII. Preparation of Transgenic Plants

The transgenic plant or plant cell expressing an RNA transcript or polypeptide of the present invention may be constructed in accordance with methods known in the art. In brief, the plant or plant cell is constructed by incorporating one or more expression constructs encoding a polypeptide of the present invention into the plant host genome and propagating the resulting modified plant or plant cell into a transgenic plant or plant cell.

In a preferred embodiment of this invention, the transgenic plants of this invention are cereal crop plants, including but not limited to, wheat, rye, triticale, barley, maize, sorghum and rice. In a more preferred embodiment, the transgenic plants are wheat, maize, barley, oats, and rye. In an alternate preferred embodiment, the transgenic plants of this invention are dicotyledonous plants.

The DNA constructs described above may be introduced into the genome of the desired plant host by a variety of conventional techniques. Techniques for transforming a wide variety of higher plant species are well known and described in the technical and scientific literature. See, for example, Weising, et al., *Ann. Rev. Genet.* 22:421–477 (1988).

The DNA construct may be introduced directly into the genomic DNA of the plant cell using techniques such as biolistic methods, electroporation, PEG poration, and microinjection of plant cell protoplasts or embryogenic callus. Alternatively, the DNA constructs may be combined with suitable T-DNA flanking regions and introduced using an *Agrobacterium tumefaciens* or *A. rhizogenes* vector.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are herein incorporated by reference), and are commercially available (e.g., the helium gas-driven microprojectile accelerator (PDS-1000/He) (BioRad).

Particle bombardment techniques are described in Klein, et al., *Nature* 327:70–73 (1987). A particularly preferred method of transforming wheat and other cereals is the bombardment of calli derived from immature embryos as described by Weeks et al., *Plant Physiol.* 102:1077–1084 (1993).

Microinjection techniques are known in the art and well described in the scientific and patent literature. The introduction of DNA constructs using polyethylene glycol precipitation is described in Paszkowski, et al., *EMBO J.* 3:2717–2722 (1984). Electroporation techniques are described in Fromm, et al., *Proc. Nat'l Acad. Sci. USA* 82:5824 (1985).

*Agrobacterium tumefaciens*-meditated transformation techniques are also well described in the scientific literature. See, for example Horsch, et al., *Science* 233:496–498 (1984), and Fraley, et al. *Proc. Nat'l Acad. Sci. USA* 80:4803 (1983). Although Agrobacterium is useful primarily in dicots, certain monocots can be transformed by Agrobacterium. For instance, Agrobacterium transformation of rice is described by Hiei, et al, *Plant J.* 6:271–282 (1994); U.S. Pat. Nos. 5,187, 073; 5,591,616; Li, et al., *Science in China* 34:54 (1991); and Raineri, et al., *Bio/Technology* 8:33

(1990). Xu, et al., *Chinese J. Bot.* 2:81 (1990) transformed maize, barley, triticale and asparagus by Agrobacterium infection.

The present invention is particularly useful in plants such as wheat and other cereals that are susceptible to diseases caused by soilborne pathogens. A number of methods of transforming cereals have been described in the literature. For instance, reliable methods for stable transformation of wheat, including the highly-regenerable cultivars such as the hard white spring wheat Bobwhite, are described (Vasil et al., *Bio/Technology* 10:667–674,1992; Vasil et al., *Bio/Technology* 11:1553–1558, 1993; Weeks et al., supra; Becker et al., *Plant J.* 5:299–307, 1994; Nehra et al., *Plant J.* 5: 285–297, 1994; Blechl and Anderson, *Nat. Biotech.* 14:875–879, 1996).

Transformed plant cells that are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the cell wall-degrading polynucleotide sequences. Plant regeneration from cultured protoplasts is described in Evans, et al., Protoplasts Isolation and Culture, Handbook of Plant Cell Culture, Macmillian Publishing Company, New York, pp. 124–176 1983; and Binding, Regeneration of Plants, Plant Protoplasts, CRC Press, Boca Raton, pp. 21–73 1985. Regeneration can also be obtained from plant callus, explants, organs, or parts thereof. Such regeneration techniques are described generally in Klee, et al. *Ann. Rev. of Plant Phys.* 38:467–486 (1987).

Transformed plants are evaluated for the presence of the desired properties and/or the extent to which the desired properties are expressed. A first evaluation may include the level of expression of the newly introduced genes, the level of protection of the transformed plants, and stable heritability of the desired properties.

One of skill will recognize that after the expression cassette is stably incorporated in transgenic plants and confirmed to be operable, it can be introduced into other plants by sexual crossing. A technique used to transfer a desired phenotype to a breeding population of plants is through backcrossing. However, any of a number of standard breeding techniques can be used, depending upon the species to be crossed.

Any plant species or variety that is subject to fungal attack may be transformed with one or more genetic constructs according to the invention in order to improve resistance to pathogens, for example, to improve resistance to soilborne root pathogens.

Preferred embodiments of the invention are transgenic plants expressing phzO genes in a root-specific manner. In a preferred embodiment biosynthetic genes for hydroxylated phenazine are expressed behind a root specific promoter to protect transgenic plants against soilborne root pathogens, for example, Rhizoctonia, Pythium, and *Gaeumannomyces graminis*, which cause a significant adverse impact on the production of important crops worldwide. It is of particular interest to protect plants from the root disease take-all, caused by *Gaeumannomyces graminis* var. *tritici* (Ggt), Rhizoctonia root rot, caused by *Rhizoctonia solani* and *R. oryzae*, and Pythium root rot caused by any of several Pythium species, notably, *Pythium ultimum* and *P. irregulare*, which are important root diseases of cereal, e.g., wheat, barley, triticale, and rye, worldwide.

As a matter of illustration the species of the following, non-limitative, list are monocots of particular interest: wheat, rice, barley, maize, rye, oat, sorghum, triticale.

Analysis of transgenic lines may be done by northern blots, in situ hybridization, RT-PCR, S1 nuclease protection assays, RNase protection assays, Western blots, enzyme assays or other methods for detection of expressed mRNA or protein.

IX. Uses

As discussed in detail above, a particular use of the invention is the provision of microorganisms transformed with a nucleic acid sequence encoding PhzO to provide strains which produce 2-hydroxylated phenazine or which produce increased amounts of 2-hydroxylated phenazine from phenazine-1-carboxylic acid. Uses of these transformed strains are as biocontrol agents for control of plant root diseases, or for production of 2-hydroxylated phenazines from exogenous phenazine-1-carboxylic acid.

The invention further encompasses antifungal compositions in which the active ingredient is the antibiotic substance produced by the recombinant biocontrol agent of the present invention or alternatively a suspension or concentrate of the microorganism. For example, biocontrol compositions containing a biologically pure culture of a transformed strain as an active biocontrol can be applied as seed or soil treatment to suppress or control phytopathogenic fungi or bacteria. Formulations and application methods using biocontrol strains are described in U.S. Pat. Nos. 4,456,684; 4,647,533; 4,940,840; 6,051,383; 5,955,298; 5,817,502; 5,756,087; 5,723,759; 5,716,849; 5,698,425; 5,679,560; and 5,662,898.

As discussed above, another particular use of the invention is the provision of plants or plant cells transformed with a nucleic acid sequence encoding PhzO to provide plants having resistance to plant pathogens.

The present invention is also directed to methods for using the polypeptides having PhzO enzyme activity to produce 2-hydroxylated phenazine compounds from phenazine-1-carboxylic acid. A specific advantage is the production in quantities large enough to enable their isolation and use. These compounds may be effective in the inhibition of growth of microbes, particularly phytopathogenic microbes.

Also, another use of the invention is as probes and primers capable of detecting a phzO gene or functional equivalents thereof.

Using the nucleic acid sequences of the invention facilitates the isolation of homologous genes from hosts to obtain genes which protect host cells, including plants against related fungal pathogens.

EXAMPLE

The following example is intended only to further illustrate the invention and is not intended to limit the scope of the invention which is defined by the claims.

Materials and Methods

Bacterial Strains and Plasmids. The bacterial strains and plasmids used in this study are described in Table 1. Rifampicin-resistant derivatives of *P. fluorescens* strains 2–79, M4-80R, Q8r1-96, and *P. chlororaphis* 30–84 (referred to here by its original designation, *P. aureofaciens* 30–84) were used. Pseudomonas strains were grown at 28° C. in Luria-Bertani (LB) broth, 2×YT broth (Sambrook et al, 1989, supra), or M9 minimal medium (Ausubel et al., *Short Protocols in Molecular Biology*, John Wiley & sons, Inc., New, N.Y.) supplemented with sodium citrate to a final concentration of 40 mM as a carbon source. *E. coli* strains were grown in LB broth or 2×YT broth at 28° C. or 37° C. To enhance phenazine production, Pseudomonas strains were grown in LB supplemented with 1.5% glucose. When appropriate, antibiotic supplements were used at the following concentrations: tetracycline, 12.5 µg/ml (*E. coli*) or 25 µg/ml (Pseudomonas); rifampicin, 100 µg/ml; kanamycin, 100 µg/ml; neomycin, 100 µg/ml (*P. fluorescens* 2–79); chloramphenicol, 35 µg/ml; and ampicillin, 100 µg/ml.

DNA Manipulations. Standard methods were used for DNA isolation, restriction enzyme digestion, agarose gel electrophoresis, and ligation (Ausubel et al., 1995, supra). Pseudomonas and *E. coli* cells were transformed by electroporation in a Bio-Rad Gene Pulser II System (Bio-Rad; Hercules, Calif.) according to Enderle et al. (*Biotechniques* 25:954–958, 1998) at settings of 25 µF for the capacitor, 200Ω resistance, and an electric field of 1.8 kV/cm. Genomic DNA was isolated and purified by a cetyltrimethylammonium bromide (CTAB) miniprep procedure (Ausubel et al., 1995, supra). For Southern blotting and hybridization, 500 ng of genomic DNA was digested with EcoRI and PstI, separated by electrophoresis in a 0.8% agarose gel, and transferred onto a BrightStar-Plus nylon membrane (Ambion, Inc., Austin, Tex.) in 0.4 M NaOH with subsequent cross-linking by exposure to ultraviolet irradiation (Ausubel et al., 1995, supra). Membranes were prehybridized for 3 h at 60° C. in a solution containing 4×SSC (1×SSC is 0.15 M NaCl plus 0.015 M sodium citrate), 4×Denhardt's solution, 0.1% SDS, and 250 mg/ml of denatured salmon sperm DNA. After prehybrization, the membranes were incubated with specific probes overnight under the same conditions and washed with 2×SSC, 0.1% SDS at room temperature, 0.2×SSC, 0.1% SDS at room temperature, 0.2×SSC, 0.1% SDS at 60° C., and 0.1×SSC, 0.1% SDS at 60° C. DNA-DNA hybrids were detected with the BrightStar non-isotopic detection kit (Ambion Inc.) according to the manufacturer's protocol. The 2.1-kb phzO probe was amplified by PCR from *P. aureofaciens* 30–84 genomic DNA with the oligonucleotide primers 30–84XBA (5'-AAG TCC AGA TGC GAA AGA ACG-3') (SEQ ID NO:5) and PHZO10 (5'-AAG TGG CAT GGC TCG AAT AAA G-3') (SEQ ID NO:6). Amplification was carried out in a 25-µl reaction mixture containing 1×Thermophilic DNA polymerase buffer (Promega Corp., Madison, Wis.), 1.5 mM $MgCl_2$, 5.0% (final) dimethyl sulfoxide (DMSO) (Sigma Chemical Co., St. Louis, Mo., 200 µM each of dGTP, dATP, dCTP, and dTTP (Perkin-Elmer, Norwalk, Conn.), 20 pM of each primer, and 1.2 U of Taq DNA polymerase (Promega Corp.). Amplifications were performed with a PTC-200 thermal cycler (MJ Research Inc., Watertown, Mass.). The cycling program included a 45-sec initial denaturation at 94° C. followed by 30 cycles of 94° C. for 45 sec, 51° C. for 45 sec, and 72° C. for 1.5 min. Amplified DNA was labeled with the Random Primer Biotin Labeling kit (NEN Life Science Products Inc., Boston, Mass.).

DNA Sequencing and Analysis. DNA was sequenced by using the ABI Prism Dye Terminator Cycle Sequencing Kit (Perkin-Elmer), according to manufacturer. All custom-designed oligonucleotides came from Operon Technologies Inc. (Alameda, Calif.). Sequence data were compiled and analyzed for open reading frames and codon usage with the Omiga 1.1.3 software package (Oxford Molecular Ltd., Oxford, UK). A database search for similar protein sequences was carried out with the BLAST (Tatusova and Madden, *FEMS Microbiol. Lett* 174:247–250, 1999) and FASTA network servers at National Center for Biotechnology Information (NCBI) and the European Molecular Biology Laboratory (EMBL), respectively. The probable domain homologies search was performed with PROSITE (EMBL, Heildelberg, Germany (Bairoch et al, *Nucleic Acids Res.* 24:189–196, 1995)) and ISREC ProfileScan (Swiss Institute for Experimental Cancer Research, Epalinges, Switzerland, URL: wwwv.isrec.isb-sib.ch/software/PFSCAN form.html) computer services. The significance of the similarity of a predicted protein to known proteins was determined by calculating the binary comparison score (Z-score). Pairwise alignments were obtained by using the BESTFIT program from the GCG package (Program Manual for the Wisconsin Package, Version 8. GCG. Madison Wis.), and the resulting percent identities, percent similarities, alignment scores (A), mean random alignment scores (R), and standard deviations (SD) (n=100) were noted. Z scores were then calculated by the equation (A–R)SD. Multiple sequence alignments were built with Omiga's ClustalW and analyzed with the TreeView 1.5.0 software package (Page, *Computer Applications in the biosciences* 12:357–358, 1996).

Mating and Screening of Transconjugants. Plasmids were mobilized from the donor strain *E. coli* S-17 (λ-pir) into Pseudomonas recipients by using a filter mating technique described by van Overbeek ("Responses of Bacterial Inoculants to Soil Conditions," Ph.D. Dissertation, 1998, University of Leiden, Leiden, The Netherlands). To counterselect *E. coli* donor cells, mating mixtures were plated on M9 agar supplemented with appropriate antibiotics and sodium citrate as a carbon source. Positive isolates were replated and screened for the presence of phenazine genes by PCR with primers PHZ1 and PHZ2. The oligonucleotide primers PHZ1 (5'-GGC GAC ATG GTC AAC GG-3') (SEQ ID NO:7) and PHZ2 (5'-CGG CTG GCG GCG TAT TC-3') (SEQ ID NO:8) were used as universal phenazine primers to amplify a 1.4-kb fragment containing parts of phzF and phzA in *P. aureofaciens* 30–84, which correspond to phzC and phzD in *P. fluorescens* 2–79. The amplification was carried out in a 15-µl reaction. The cycling program included an initial denaturation for 2 min at 94° C. followed by 25 cycles of 94° C. for 1 min, 56° C. for 45 sec, 72° C. for 1.75 min, and a final extension at 75° C. for 1 min. The oligonucleotide primers PHZX (5'-TTT TTT CAT ATG CCT GCT TCG CTT TC-3') (SEQ ID NO:9) and PHZY (5'-TTT GGA TCC TTA AGT TGG AAT GCC TCC G-3') (SEQ ID NO:10), were used to distinguish between the phenazine operons of *P. aureofaciens* 30–84 and *P. fluorescens* 2–79. These primers amplify a 1.1-kb DNA fragment containing parts of phzX and phzY from strain 30–84, but not from the corresponding, homologous phzA and phzB sequences of strain 2–79. The program included an initial denaturation at 94° C. for 1.5 min followed by 30 cycles of 94° C. for 45 sec, 58° C. for 30 sec, 72° C. for 1.75 min, and a final extension at 72° C. for 1 min.

Protein Expression. The *P. aureofaciens* 30–84 phzO gene was expressed under the control of the lac promoter in the plasmid vector pUCP26. *E. coli* JM109 harboring pUCP26, pUCP2.9XP, or pUCP4.5 was grown in LB to an $OD_{600}$ of 0.6 and induced with 0.5 mM isopropyl-β-D-thiogalactopyranoside (IPTG). Cells were harvested 3 h later, and total cellular protein was analyzed by electrophoresis in a 10% sodium dodecyl sulfate-polyacrylamide gel (SDS-PAGE) as described by Copeland (*Methods for Protein Analysis*, Chapman & Hall, New York, N.Y., pp. 62–71, 1994).

Alternatively, phzO was amplified by PCR from *P. aureofaciens* 30–84 genomic DNA with the primers PHZO start (5'-CGA CTC TAG AAC GTT GTC CTT GAC C-3') (SEQ ID NO:1) and PHZO10 in a 30-1 reaction mixture with a cycling program that included a 45-sec initial denaturation at 94° C., 29 cycles of 94° C. for 45 sec, 56° C. for 45° C. sec, and 72° for 3.25 min. The 1.8-kb reaction product was ligated into pGEM-T Easy (Promega) to give pGEM-PHZO, which was transformed into E. coli JM109. The resulting plasmid, pGEM-PHZO, contained the entire phzO gene preceded by 82 bp upstream of the start codon and 265 bp downstream of the coding sequence. Expression was induced as above.

PCA Transformation Assay. E. coli JM109 bearing pUCP26 or pUCP2.9XP was grown at 37° C. in 2×YT supplemented with tetracycline. The cells were harvested, suspended in fresh media, and induced with 0.5 mM IPTG. PCA was added to a final concentration of 0.3 or 0.5 mg/ml from a 25 mM stock solution in 5% (w/v) NaHCO$_3$. Samples were taken at 3-h intervals, extracted, and analyzed for phenazine composition by reverse-phase high performance liquid chromatography (RP-HPLC).

Gene Replacement Mutagenesis of phzO. A phzO knockout mutant of P. aureofaciens 30–84 was generated by gene replacement as described by Schweizer (Mol. Microbiol. 6:1195–1204, 1992). Briefly, a 2.5-kb PvuII fragment bearing a tetracycline resistance gene from pALTER-Ex1 (Promega) was inserted into phzO at the NcoI site. The interrupted gene was subcloned into pNOT19, yielding pOT1, which was digested with NotI and ligated with a 5.3-kb pMOB3 sacB cassette. The resulting plasmid, pOT1-1, was mobilized into P. aureofaciens 30–84 from E. coli S-17 (λ-pir) and double crossover progeny were selected as described previously (Schweizer, 1992, supra).

Analysis of Phenazine Compounds. Phenazine compounds were extracted according to Bonsall et al. (i Appl. Environ. Microbiol. 63:951–955, 1997). Bacterial strains were cultivated for 72 h in LB broth supplemented with 1.5% glucose. The cultures were acidified with 10% trifluoroacetic acid (TFA) and then extracted twice with ethyl acetate. The organic phase containing the phenazines was evaporated to dryness and suspended in 35% acetonitrile (ACN)/0.1% TFA.

Since phenazine-producing Pseudomonas spp. often produce mixtures of phenazine compounds, a generalized HPLC protocol for detection of these metabolites was developed. The protocol utilized a NOVA-PAK C$_{18}$reverse-phase Radial-PAK cartridge (4 μm, 8×100 mm) (Waters Corp., Milford, Mass.), and solvent conditions consisting of a 2-min initial wash with 35% ACN/0. 1% TFA in H$_2$O followed by a 25-min linear gradient to 100% ACN/0.1% TFA at a flow rate of 1.0 ml/min. The Waters HPLC system included a 710B WISP, 510 pumps, and a 680 automated gradient controller with a 990 photodiode array detector (Waters Corp.). Phenazine compounds were identified by retention time and ultraviolet spectrum. Standards included compounds purified from well-characterized strains (Mavrodi et al, 1998, supra; Pierson and Thomashow, 1992, supra) and chemically-synthesized compounds (PCA, 2-OH-PCA, and 2-OH-PHZ) obtained from Colour Your Enzyme (Bath, Ontario, Canada). Although the protocol allowed simultaneous identification of phenazine compounds including unsubstituted phenazine, PCA, 2-OH-PCA, 2-OH-PHZ, chlororaphin, and 1-OH-PCA, it failed to clearly separate PCA and 2-OH-PCA. 2-OHPHZ, which is formed by spontaneous decarboxylation of 2-OH-PCA (see below), was therefore used as an indicator of 2-hydroxyphenazine synthesis and when necessary, the presence of 2-OH-PCA in samples containing PCA was determined by peak purity and spectral analyses using the Waters 991 photodiode array (Waters Corp.).

Fungal Inhibition Assay. The inhibition of hyphal growth of Gaeumannomyces graminis var. tritici by Pseudomonas strains 30–84, 30–84mxO, 2–79, and 2–79 harboring pUCP2.9XP was assayed as described by Ownley et al. (Phytopathology 82:178–184, 1992) on Kanner agar supplemented with potato extract (KMPE), which supports the production of phenazine compounds. Plates were incubated at room temperature in the dark and radial growth of the fungus was measured after 5 days. The experiment was repeated twice with 7 or 8 replicates each time. Inhibition of mean fungal radial growth by each bacterial strain was analyzed for significance by the Student t-Test at P=0.05.

Nucleotide Sequence Accession Number. The nucleotide sequence for the phzO gene is listed in the GenBank computer database under accession number AF230879.

RESULTS

Localization of the 2-Hydroxyphenazine Gene. Previous studies by Pierson and Thomashow, Mol. Plant-Microbe Interact. 5:330–339, 1992, identified two cosmids, pLSP259 and pLSP282, from a genomic library of P. aureofaciens 30–84 that were able to restore Phz$^-$ mutants of 30–84 to production of PCA, 2-OH-PCA, and 2-OH-PHZ. These cosmids contain identical 11.2-kb and 9.2-kb EcoRI fragments, and an additional 3.8-kb EcoRI fragment is present in pLSP282 (FIG. 1). To determine whether pLSP259 and pLSP282 are sufficient to enable the synthesis of PCA, the two hydroxyphenazines, or all three products, each cosmid was introduced into P. fluorescens strains 2–79, M4-80R, and Q8r1-96, and its presence confirmed by PCR with phzXY-specific primers. Phenazine compounds produced by the transformed strains were extracted and analyzed by RP-HPLC. Transformants of all three strains harboring either cosmid produced both PCA and the 2-hydroxyphenazines (Table 2), indicating that pLSP259 and pLSP282 contain the necessary information required for the synthesis of all three compounds.

We next determined whether the core phenazine operon, phzXYFABCD, present in both cosmids was sufficient for the synthesis of the three phenazine products. Previous studies (Pierson et al., 1995, supra) had suggested that in P. aureofaciens 30–84, the C-terminal 28 amino acids of PhzC were necessary for the synthesis of 2-OH-PCA and 2-OH-PHZ. PhzC is a 278-amino acid, 30.3-kD protein with 94% amino acid sequence identity to PhzF from P. fluorescens 2–79. These proteins have no motifs or similarities to other proteins of known function, but PhzF is absolutely required for the synthesis of PCA in strain 2–79 (Mavrodi et al., 1998, supra). A pairwise alignment of the terminal 28 amino acids of the two proteins revealed three conservative substitutions: lysine at position 251 in strain 30–84 instead of arginine in strain 2–79; glutamic acid at position 257 instead of aspartic acid; and valine at position 269 instead of isoleucine. To determine the biosynthetic potential of phzXYFABCD, the core operon was cloned downstream of a tac promoter and transposed from pUT-Km/30–84 into the genomes of P. fluorescens 2–79, Q8r1-96, and M4-80R. Transposition in each recipient was confirmed by PCR with phzXY-specific primers. RP-HPLC revealed that all three transformed strains produced PCA but not 2-OH-PCA or 2-OH-PHZ (Table 2), indicating that the core genes from strain 30–84 do not contain the information necessary for the synthesis of 2-hydroxyphenazine compounds.

The regions ;upstream and downstream phzXYFABCD were next analyzed for genes responsible for the conversion of PCA to 2-hydroxyphenazine derivatives. P. fluorescens 2–79 harboring either pLSP282Δ30-8, containing the 3.8-kb and 11.2-kb EcoRI fragments 5' to the phz operon, or pLSP282Δ30-8, containing the 11.2 kb fragment (Pierson and Thomashow, 1992, supra) (FIG. 1) produced only PCA, suggesting that the genes required for hydroxyphenazine synthesis do not reside upstream of the core locus. The remaining 4.5-kb fragment downstream of the phenazine operon in pLSP282 was cloned into the broad host vector pUCP26. A smaller 2.9 kb XbaI-PstI fragment also was cloned into pUCP26 in the opposite orientation. Plasmid pUCP2.9XP contained the C-terminal region of phzD and downstream sequences under the control of the vector's lac promoter. Both plasmids were introduced into P. fluorescens 2–79 and the phenazines were extracted for RP-HPLC analysis. Strain 2–79 containing pUCP2.9XP, but not pUCP4.5, produced 2-OH-PHZ in addition to the PCA (FIG. 2), indicating that the 2.9-kb DNA fragment lacked a promoter, was colinear with the phenazine biosynthetic locus, and contained the gene(s) required for the conversion of PCA.

DNA Sequence Analysis. The 2.9-kb XbaI-PstI fragment from Ps. 30–84 was sequenced in both directions and compiled in Omiga. Computer analysis revealed a large open reading frame, designated phzO, located 271 nucleotides downstream from phzD, and preceded by a well-conserved potential ribosome binding site, GAGG. phzO encoded a 491-amino acid protein with a calculated molecular mass of 55.1 kDa. Homology searches with the deduced amino acid sequence revealed similarity to bacterial aromatic hydroxylases and monooxygenases (Table 3). Phylogenetic analysis of these aligned protein sequences resulted in the tree shown in FIG. 3. The high bootstrap values (from 1,000 resamplings) showed the robustness of these groups.

Figure 2:
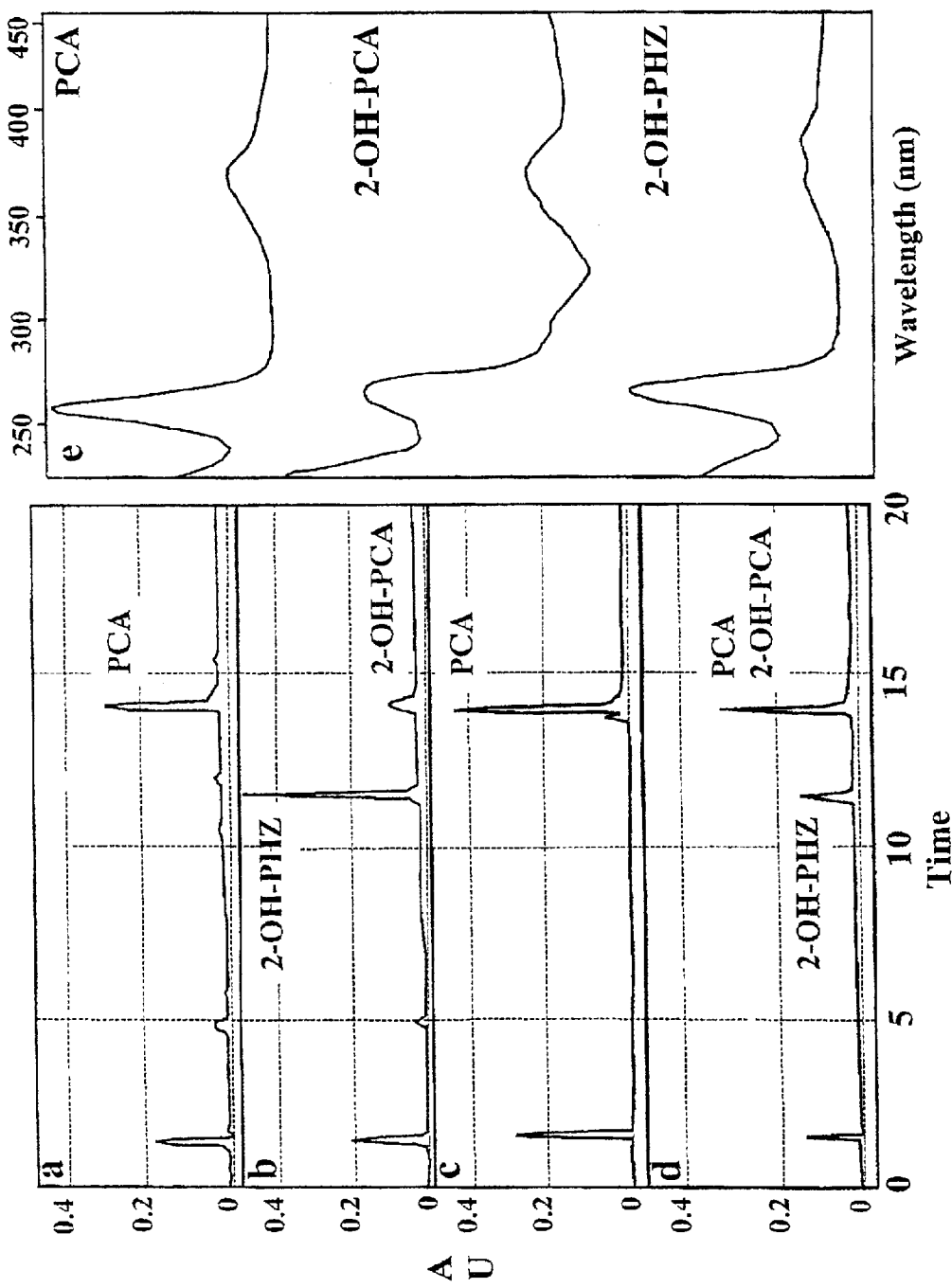
FIG. 2 shows the HPLC analyses of phenazine compounds produced by *P. fluorescens* 2–79 harboring the pUCP26 (vector) (A); *P. fluorescens* 2–79 harboring pUCP2.9XP, containing phzO (B); *E. coli* JM109 harboring pUCP26 (C); *E. coli* JM109 harboring pUCP2.9XP (D); and peak identity of PCA, 2-OH-PCA, and 2-OH-PHZ confirmed by spectral analysis (E). Retention times for PCA and 2-OH-PHZ are 14.1 min and 11.4 min, respectively. Absorption maxima for PCA are 248 nm and 371 nm. Absorption maxima for 2-OH-PCA are 257 nm and 369 nm. Absorption maxima for 2-OH-PHZ are 257 nm, 368 nm, and 387 nm.

Expression and Functional Analysis of PhzO. The phzO gene from P. aureofaciens 30–84 was cloned in pUCP26 under the control of the lac promoter and expressed in E. coli JM109. Cells from induced cultures expressing PhzO produced a unique band of approximately 55 kDa on SDS-PAGE gels, in good agreement with the size predicted by nucleotide sequence analysis. Induced cultures of E. coli expressing PhzO converted PCA (0.3 or 0.5 mg/ml in 5% $NaHCO_3$) to 2-OH-PCA and 2-OH-PHZ within 3 h, whereas no such conversion occurred in control cultures harboring only pUCP26 (FIG. 2). These results indicate that PhzO, independent of up- and downstream sequences, is sufficient to hydroxylate PCA. To determine whether PhzO is responsible for this reaction in P. aureofaciens 30–84, a tetracycline resistance gene was inserted into phzO and introduced in the genome by homologous recombination. P. aureofaciens 30–84mxO produced PCA but not 2-OH-PCA and 2-OH-PHZ. Finally, to test the hypothesis that the conversion of 2-OH-PCA to 2-OH-PHZ occurs spontaneously, in the absence of enzymatic activity, as suggested previously (Flood et al., supra), solutions of synthetic 2-OH-PCA were incubated for 18 h in 0.1 M sodium phosphate buffer at pH 4.0, 6.0, 7.0, and 8.0, extracted, and analyzed by RP-HPLC. At pH 4.0, 2-OH-PHZ accounted for only 0.2% of the total phenazine present after 18 h, but at pH 6.0, 7.0, and 8.0, 33.3%, 74%, and 64% of the 2-OH-PCA initially present was converted to 2-OH-PHZ.

Conservation of PhzO Among Phenazine-Producing Fluorescent Pseudomonas spp. A 2.1-kb probe containing the 1.5-kb phzo gene and flanking regions was hybridized to total genomic DNA from 20 known phenazine-producing fluorescent pseudomonads to determine whether the gene is unique to producers of 2-hydroxyphenazines or if it also is conserved in other phenazine-producing strains. All seven strains of P. aureofaciens contained sequences that hybridized to the probe (FIG. 5), and each produced 2-OH-PCA and 2-OH-PHZ in addition to PCA as determined by RP-HPLC. Two additional strains, P. chlororaphis 9446 and P. aeruginosa 25011, contained a faintly-hybridizing band. However, no 2-hydroxylated phenazines were found in the extracts from cultures of these strains (data not shown), which previously were reported to produce chlororaphin and aeruginosins A and B, respectively (Johnson and Palleroni, 1989, supra; Yabuuchi and Ohyama, Int. J. Syst. Bacteriol. 22:53–64, 1972). No hybridization was detected between the phzO probe and DNA from P. chlororaphis strains ATCC 17411 and ATCC 17809, P. aeruginosa strains PA01, PAK-N1, PAK-NP1, PAK-NP2, ATCC 25007 and ATCC 25011, or the PCA-producing P. fluorescens strains 2–79, UQ 112, UN 4127, and UN 15 (FIG. 5), even after very heavy overexposure of the films (data not shown).

Fungal Inhibition Assays. Assays were conducted in vitro to determine if strains producing hydroxyphenazine compounds inhibited the hyphal growth of G. graminis var. tritici more than those producing only PCA. The radial growth of the fungus on plates in the presence of strain 30–84 was significantly less than that in the presence of the mutant 30–84mxO, which produced only PCA (18 vs. 22 mm, $P \geq 0.05$). Similarly, P. fluorescens 2–79(pUCP2.9XP), transformed to hydroxyphenazine production, was more inhibitory than wild-type 2–79 (14 vs. 17 mm, $P \geq 0.05$).

Figure 5:
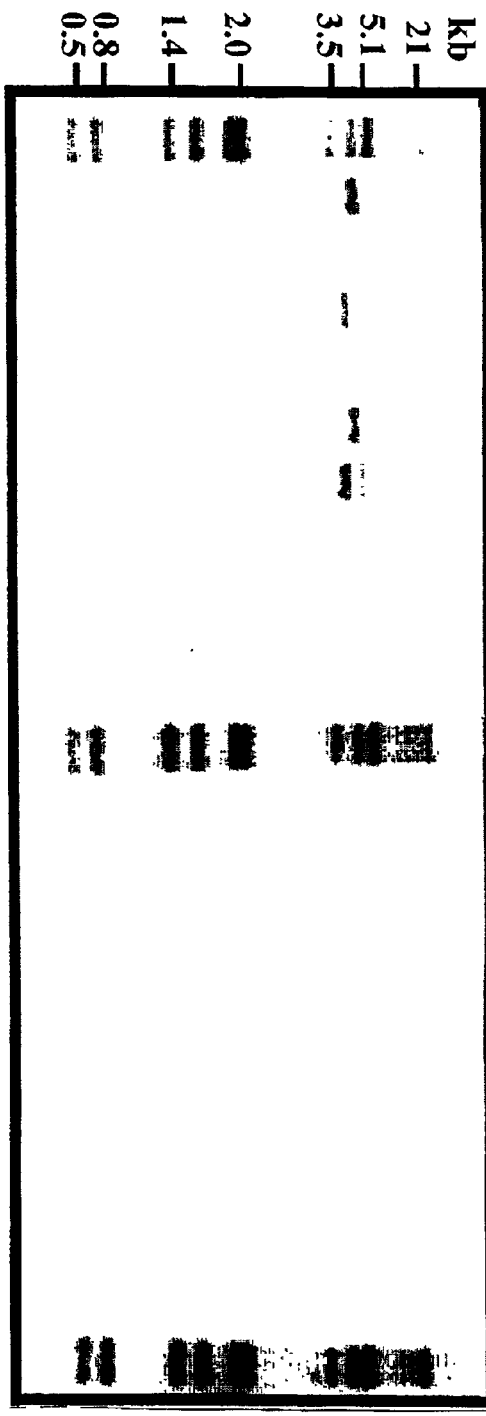
FIG. 5 shows Southern hybridization of the phzO probe to total genomic. DNA from twenty phenazine-producing Pseudomonas strains. Total DNA samples were digested with endonucleases PstI and EcoRI.

Screening. We screened a collection of phenazine-producing Pseudomonas spp. for the presence of phzO by Southern hybridization (FIG. 5). Our results indicate that this gene is found almost exclusively in isolates of P. aureofaciens. The only two non-P. aureofaciens strains that hybridized with the phzO probe were P. chlororaphis 9446 and P. aeruginosa 25011 (FIG. 5). However, it is possible that these strains do not have the phzO homologue, since in both cases the hybridization signal was very weak, the size of the hybridizing fragment was different from that in P. aureofaciens strains, and no hydroxylated phenazines were detected in the culture extracts. Based on these findings, we speculate that phzO is a species-specific gene in fluorescent Pseudomonas spp. Moreover, the fact the all the tested strains possess a well-conserved core phenazine locus (D. M. Mavrodi and L. S. Thomashow, unpublished), may indicate that the acquisition of phenazine-modifying genes by phenazine-producing pseudomonads is a fairly recent event.

Biocontrol Activity. Interest in strains of P. aureofaciens frequently has centered on their ability to suppress soilborne plant pathogens (Becker et al. Phytopathology 80:206–211, 1990; Person and Thomashow, 1992, supra; Smirnow and Kiprianova, Bacteria of Pseudomonas Genus, Naukova Dumka, Kiev, Ukraine, pp. 100–111, 1990 (translation by D. V. Mavrodi; Thomashow and Weller, J. Bacteriol. 170:3499–3508, 1988). We used derivatives of strain 30–84 mutated in phzO, and 2–79 transformed with phzO, to evaluate the importance of hydroxylated phenazines in biological control activity against G. graminis var. tritici in vitro. For both strains, the ability to produce hydroxyphenazine compounds was correlated with greater antifungal activity than was production of PCA alone. These results are consistent with the findings of Smimov, 1990 supra, who compared the inhibitory effects of PCA, 2-OH-PCA, and 2-OH-PHZ against a variety of bacterial and fungal animal and plant pathogens and found that in all cases the 2-hydroxyphenazines exhibited stronger bacteriostatic and fungistatic activity. We have recently demonstrated that the introduction of the core biosynthetic genes in other biocontrol microorganisms resulted in increased suppression of certain phytopathogenic fungi (Huang et at., unpublished; Timms-Wilson et al., unpublished). The phzO gene from P. aureofaciens 30–84 is an attractive target for such genetic manipulations because of the wide antimicrobial and antifungal activity of 2-hydroxyphenazines, which, on the other hand, are harmless to fish, insects, or mammals (Nelson and Toohey, U.S. Pat. No. 3,367,765, Chemical Abstracts 68:77160, 1968; Toohey et al., Can. J. Bot. 43:1151–1155, 1965).

TABLE 1

Bacterial strains and plasmids used in this study.

| Strain | Description[a] | Reference or source |
|---|---|---|
| *P. aeruginosa* | | |
| PAO1 | Phz[+], produces pyocyanin | Essar et al. |
| ATCC 25007 | Phz[+], produces pyocyanin, aeruginosins A and B | Smirnov et al. |
| ATCC 25011 | Phz[+], produces aeruginosins A and B | Xun et al. |
| KN-1 | Phz[+], produces pyocyanin | Laboratory collection |
| KNP-1 | Phz[+], produces pyocyanin | Laboratory collection |
| KNP-2 | Phz[+], produces pyocyaliin | Laboratory collection |
| *P. aureofaciens* [synonym: *P. chlororaphis*] | | |
| 30-84 | Phz[+], produces PCA, 2-OH-PCA, and 2-OH-PHZ | Pierson et al., 1992 |
| 30-84 mxO | Phz[+], produces PCA | This study |
| ATCC 13985 | Phz[+], produces PCA, 2-OH-PCA, and 2-OH-PHZ | Smirnov et al. |
| BS 1391 | Phz[+], produces PCA, 2-OH-PCA, and 2-OH-PHZ | V. Kotchetkov |
| BS 1393 | Phz[+], produces PCA, 2-OH-PCA, and 2-OH-PHZ | V. Kotchetkov |
| PGS12 | Phz[+], produces PCA, 2-OH-PCA, and 2-OH-PHZ | Georgakopoulos et al. Appl. Environ. Microbiol. 60: 2931–2938, 1994 |
| AP-9 | Phz[+], produces PCA, 2-OH-PCA, and 2-OH-PHZ | Aprill, MS Thesis, WSU, 1986 |
| TX-1 | Phz[+], produces PCA, 2-OH-PCA, and 2-OH-PHZ | Eco-Soils Systems |
| *P. chlororaphis* | | |
| ATCC 17411 | Phz[+], produces chlororaphin | Turner et al. 1986 |
| ATCC 17809 | Phz[+], produces chlororaphin | ATCC |
| ATCC 9446 | Phz[+], produces chlororaphin | Smirnov et al. 1990 |
| *P. fluorescens* | | |
| 2-79 | Phz[+], Rif[r], produces PCA | Weller, Phytopathology 73:1548–1553, 1983 |
| M4-80R | Phz[-], Rif[r] | Hamdan et al., Appl Environ Microbiol. 57–3270–3277, 1991 |
| Q8r1-96 | Phl[+], Rif[r] | Raaijmakers et al., Mol. Plant-Microbe Interact. 11:144–152, 1998 |
| UQ112 | Phz[+], produces PCA | G. Botelho |
| UN15 | Phz[+], produces PCA | G. Botelho |
| UN4127 | Phz[+], produces PCA | G. Botelho |
| *E. coli* | | |
| SM17 (λ-pir) | thi pro hsdR hsdM recA rpsL RP4-2 Tet[r]::Mu, Kan[r]::Tn7 | Simon et al., Bio-technology 1:784–791, 1983 |
| JM109 | F' traD36proA+ proB+ lacI lacZΔM15/recA1 | Promega Corp. |
| Plasmids | | |
| pALTER-Ex1 | ColE1 Tet[r] SP6, tac, and T7 promoters | Promega Corp. |
| pNOT19 | ColE1 bla accessory plasmid | Schweizer; supra |
| pUCP26 | pUCP18-derived broad-host-range vector Tet[r] | West et al. Gene 128:81–86, 1994 |
| pMOB3 | Kan[r] cat sacBR | Schweizer, supra |
| pUCP4.5 | pUCP26 containing 4.5 kb XbaI-EcoRI DNA fragment from *P. aureofaciens* 30-84, Tet[r] | This study |
| pUCP2.9XP | pUCP26 containing 2.9 kb XbaI-PstI DNA fragment from *P. aureofaciens* 30-84; contains phzO, Tet[r] | This study |
| pGEM-T Easy | Amp[r], pUC18-derived SP6 and T7 promoters, f1 ori, lacZalpha | Promega Corp. |
| pGEM-PHZO | pGEM-T Easy containing 1.8-kb phzO fragment amplified from *P. aureofadens* 30-84 by PCR | This study |
| p18Sfi | Amp[r], pUCP18-derived vector with SfiI-EcoRI-SalI-HindIII-SfiI as multiple cloning site | Herrero et al., J. Bacteriol. 172: 6557–6567, 1990 |
| pUT-Km-Tn5 | Amp[r], Tn-5-based delivery plasmid with Kan[r] | Herrero et al. |
| pUT-Km/30-84 | pUT-Km-Tn5 with phz XYFABCD from *P. aureofaciens* 30-84 cloned between SfiI sites | This study |
| pLAFR3 | IncP Tet[r] cos[+] rlx[+] | Staskawicz et al., J. Bacteriol 169: 5789–5794, 1987 |
| pLSP259 | pLAFR3 containing 20.9 kb DNA fragment from *P. aureofaciens* 30-84; Tet[r] | Pierson et al., 1992 |
| pLSP282 | pLAFR3 containing 24.7 kb DNA fragment from *P. aureofaciens* 30-84; Tet[r] | Pierson et al., 1992 |
| pLSP282Δ20-9 | pLAFR3 containing 15.0 kb DNA fragment from *P. aureofaciens* 30-84; Tet[r] | Pierson et al., 1992 |
| pLSP282Δ30-8 | pLAFR3 containing 11.2 kb DNA fragment from *P. aureofaciens* 30-84; Tet[r] | Pierson et al., 1992 |
| pNOT2.9T-1 | pNOT19 containing 2.9 kb XbaI - PstI DNA fragment from *P. aureofaciens* 30-84; Tet resistance gene inserted at NcoI in same orientation as phzO; Tet[r], Amp[r] | This study |
| pOT-1 | 2.5 kb EcoRI-NotI DNA fragment from pNOT2.9T-1 in pNOT19; phzO[+], Tet[r], Amp[r] | This study |
| pOT1-1 | pOT-1 containing 5.6 kb sac genes from pMOB3; phzO+, Tet[r], Amp[r], Cam[r] | This study |

[a]Phz[+/−], the strain does (+) or does not (−) produce phenazines; Phl[+] production of 2,4-diacetyl-phloroglucinol; PCA, phenazine-1-carboxylic acid; 2-OH-PCA, 2-hydroxyphenazine-1-carboxylic acid; 2-OH-PHZ, 2-hydroxyphenazine; bla, β-lactamase; cat, chloramphenicol acetyltransferase; Amp[r], ampicillin resistance; Cam[r], chloramphenicol resistance; Kan[r], kanamycin resistance; Rif[r], rifampicin resistance; Tet[r], tetracycline resistance.

TABLE 2

Phenazine production as result of introduction of plasmids into *P. fluorescens* strains.

| | | Recipient *P. fluorescens* strain | | |
|---|---|---|---|---|
| Plasmid | Phenazine | 2-79 | Q8r1-96 | M4-80R |
| pLSP282 | PCA | + | + | + |
| | 2-OH-PHZ | + | + | + |
| pLSP259 | PCA | + | + | + |
| | 2-OH-PHZ | + | + | + |
| pUT-Km30-84 | PCA | + | + | + |
| | 2-OH-PHZ | − | − | − |
| pLSP282Δ20-9 | PCA | + | N/A | N/A |
| | 2-OH-PHZ | − | | |
| pLSP282Δ30-8 | PCA | + | N/A | N/A |
| | 2-OH-PHZ | − | | |

TABLE 2-continued

Phenazine production as result of introduction of plasmids into *P. fluorescens* strains.

| Plasmid | Phenazine | Recipient *P. fluorescens* strain | | |
|---|---|---|---|---|
| | | 2-79 | Q8r1-96 | M4-80R |
| pUCP4.5 | PCA | + | N/A | N/A |
| | 2-OH-PHZ | − | | |
| pUCP2.9 | PCA | + | N/A | N/A |
| | 2-OH-PHZ | + | | |

TABLE 3

Proteins displaying similarity to PhzO.

| Organism | Protein name | Enzyme | NCBI accession # | Identity (%)[a] | Similarity (%)[a] | Z-score[a] |
|---|---|---|---|---|---|---|
| *Bacillus thermoleovorans* A2 | PheA | Phenol hydroxylase | AAC38324 | 28.1 | 37.9 | 42.1 |
| *Klesbiella pneumoniae* | HpaA | 4-hydroxyphenylacetate-3-hydroxylase | AAC37120 | 24.8 | 36.5 | 44.0 |
| *Eschericha coli* ATCC 1105 | HpaB | 4-hydroxyphenylacetate hydroxylase | CAA52321 | 25.2 | 36.5 | 35.8 |
| *Ralstonia pickettii* DTP0602 | HadA | Chlorophenol-4-hydroxylase | BAA13105 | 26.7 | 39.9 | 64.4 |
| *Pseudomonas aeruginosa* PAO1 | PvcC | 4-hydroxylphenylacetate hydroxylase | AAC21673 | 24.5 | 35.5 | 61.8 |
| *Burkholderia cepacia* AC1100 | TftD | Chlorophenol-4-monooxygenase | AAC23548 | 25.1 | 37.1 | 65 |
| *Photorhabdus luminescens* | HpaB | 4-hydroxylphenylacetate hydroxylase | AAC08739 | 24.0 | 35.9 | 37 |

[a]Identities, similarities, and Z-scores were determined by the program BESTFIT from the GCG package It is understood that the foregoing detailed description is given merely by way of illustration and that modification and variations may be made within, without departing from the spirit and scope of the invention. All publications, patents, patent applications, and GenBank sequence listings cited herein are hereby incorporated by reference in their entirety.

What is claimed is:

1. An isolated nucleic acid molecule encoding a polypeptide having PhzO activity selected from the group consisting of:
   (a) a nucleotide sequence as given in SEQ ID NO:1 from nucleotide 76 to nucleotide 1564 or from nucleotide 89 to nucleotide 1564;
   (b) a nucleotide sequence encoding a polypeptide having PhzO activity comprising an amino acid sequence of SEQ ID NO:2;
   (c) a nucleic acid sequence having at least 50% nucleotide sequence identity with SEQ ID NO:1 from nucleotide 89 through nucleotide 1564 and wherein said nucleic acid sequence encodes a polypeptide having PhzO activity;
   (d) a nucleic acid sequence encoding a polypeptide having an amino acid sequence which has at least 60% sequence identity with SEQ ID NO:2 and wherein said encoded polypeptide has PhzO activity;
   (e) a nucleic acid sequence which hybridizes under medium or high stringency conditions with the nucleotide sequence of SEQ ID NO:1 from nucleotide 89 through nucleotide 1564 and wherein said DNA sequence encodes a polypeptide having PhzO activity; and
   (f) a subsequence of (a), (b), (c), (d) or (e) wherein the subsequence encodes a polypeptide fragment which has PhzO activity.

2. The nucleic acid molecule of claim 1 as shown in SEQ ID NO:1.

3. The nucleic acid molecule of claim 1 which is contained in plasmid pUCP2.9XP or plasmid pGEM-PHZO.

4. A nucleic acid construct comprising a nucleic acid molecule of claim 1 operably linked to one or more control sequences which direct the production of a polypeptide having PhzO activity in an expression host.

5. A cell transformed with the isolated nucleic acid molecule of claim 1.

6. A microorganism transformed with the isolated nucleic acid molecule of claim 1.

7. The microorganism of claim 6 wherein the microorganism is a strain of the genera selected from the group consisting of Escherichia, Enterobacter, Klebsiella, Serratia, and Pseudomonas.

8. A method for producing a polypeptide having PhzO activity in a recombinant host, comprising the steps:
 a transforming a host with one or more nucleic acid molecules of claim 1; and
 growing said host under conditions which allow biosynthesis of PhzO in said host.

* * * * *